(12) United States Patent
Ring et al.

(10) Patent No.: US 9,880,179 B2
(45) Date of Patent: Jan. 30, 2018

(54) METHOD FOR SELECTING AGENTS THAT BIND TO TRANSMEMBRANE RECEPTORS IN A CONFORMATIONALLY SELECTIVE MANNER

(71) Applicant: The Board of Trustees of the Leland Stanford Junior University, Stanford, CA (US)

(72) Inventors: Aaron Michael Ring, Palo Alto, CA (US); Aashish Manglik, Menlo Park, CA (US); Andrew Kruse, Roslindale, MA (US); Brian Kobilka, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 166 days.

(21) Appl. No.: 14/761,911

(22) PCT Filed: Feb. 5, 2014

(86) PCT No.: PCT/US2014/014892
§ 371 (c)(1),
(2) Date: Jul. 17, 2015

(87) PCT Pub. No.: WO2014/124020
PCT Pub. Date: Aug. 14, 2014

(65) Prior Publication Data
US 2015/0355200 A1  Dec. 10, 2015

Related U.S. Application Data
(60) Provisional application No. 61/761,136, filed on Feb. 5, 2013.

(51) Int. Cl.
*G01N 33/74* (2006.01)
*G01N 33/68* (2006.01)
*C07K 14/705* (2006.01)
*G01N 33/566* (2006.01)

(52) U.S. Cl.
CPC .......... *G01N 33/74* (2013.01); *C07K 14/705* (2013.01); *C07K 14/70571* (2013.01); *G01N 33/566* (2013.01); *G01N 33/6842* (2013.01); *G01N 2333/726* (2013.01); *G01N 2570/00* (2013.01)

(58) Field of Classification Search
CPC .. G01N 33/566; G01N 33/6842; G01N 33/74; G01N 2333/726; G01N 2570/00; C07K 14/705; C07K 14/70571
See application file for complete search history.

(56) References Cited

U.S. PATENT DOCUMENTS

| 7,160,541 | B2 * | 1/2007 | Springer | C07K 14/70546 424/144.1 |
| 9,453,065 | B2 * | 9/2016 | Steyaert | C07K 14/705 |
| 2003/0235863 | A1 | 12/2003 | Skylar et al. | |
| 2004/0043420 | A1 * | 3/2004 | Fowlkes | G01N 33/566 435/7.1 |
| 2011/0027910 | A1 | 2/2011 | Weir et al. | |
| 2011/0076752 | A1 | 3/2011 | Wu et al. | |

OTHER PUBLICATIONS

Kobilka BK and Deupi X. Trends in Pharmacological Sciences. 28(8):397-406. 2007. Available online at—doi 10.1016/j.tips.2007. 06.003.*
Rosenbaum DM, et al. Nature. 459(21):356-363. May 21, 2009. Available online at—doi:10.1038/nature08144.*
Sarkar CA, et al. PNAS. 105(39):14808-14813. Sep. 30, 2008. Available online at—doi/10.1073/pnas.0803103105.*
Gupta A, et al. The Journal of Biological Chemistry. 282(8):5116-5124. Feb. 23, 2007. Available online at—doi 10.1074/jbc. M609254200.*
Bohme I and Beck-Sickinger AG. Cell COmmunication and Signaling. 7(16).1-22. 2009. Available online at doi:10.1186/1478-811X-7-16.*
Park JH, et al. Nature. 454(7201):183-187. Jul. 10, 2008. Available online at—doi:10.1038/nature07063.*
Granier S, et al. Nature. 485(7398):400-404. May 16, 2012. Available online at—doi:10.1038/nature11111.*
Yao X, et al. Nat Chem Biol. 2(8):417-422. Aug. 2006. Available online at—doi:10.1038/nchembio801.*
Weib, H. Markus et al., Purification and characterization of the human adenosine A2a receptor functionally expressed in *Escherichia coli*, Eur. J. Biochem. 269, 82-92 (2002), MRC Laboratory of Molecular Biology, Hills Road, Cambridge, UK.

* cited by examiner

*Primary Examiner* — Robert Landsman
(74) *Attorney, Agent, or Firm* — James S. Keddie; Bozicevic, Field & Francis LLP

(57) ABSTRACT

Provided herein are several methods for selecting agents that bind to transmembrane receptors in a conformationally-selective way. In some embodiments, the method may comprise producing: a transmembrane receptor in an active conformation; and said transmembrane receptor in an inactive conformation and using cell sorting to select, from a population of cells comprising a library of cell surface-tethered extracellular capture agents, cells that are specifically bound to either the transmembrane receptor in its active conformation or the transmembrane receptor in its inactive conformation, but not both. In other embodiments, the method may comprise: contacting a GPCR with a population of cells that comprise a library of surface-tethered extracellular proteins; labeling the cell population with a conformationally-specific binding agent, e.g., a G-protein or mimetic thereof; and using cell sorting to select from the cell population cells that bind to the agent.

30 Claims, 18 Drawing Sheets

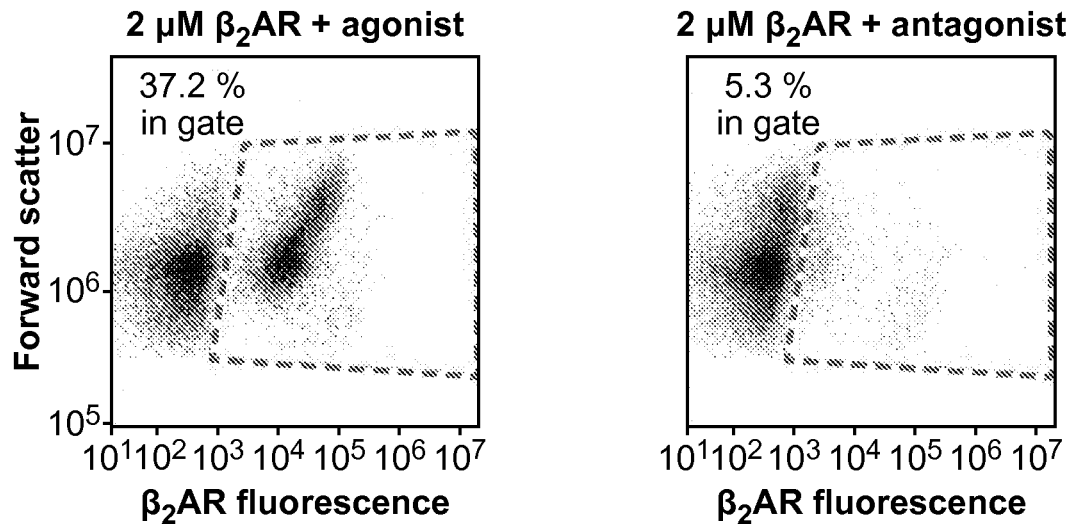
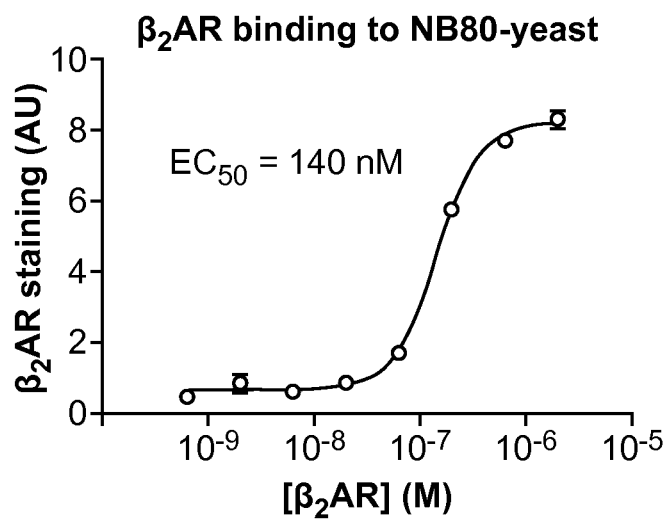
FIG. 5

| Mutation # | Residue | Degen. Codon | Possible A.A. |
|---|---|---|---|
| 1 | S29 | RSC | S/T/A/G |
| 2 | F31 | YWC | F/Y/H/L |
| 3 | S32 | RST | S/T/A/G |
| 4 | I33 | NTC | F/I/L/V |
| 5 | T35 | RYC | T/I/V/A |
| 6 | A52 | RYT | T/I/V/A |
| 7 | H54 | YWT | F/Y/H/L |
| 8 | S58 | WMC | S/N/T/Y |
| 9 | N60 | NAC | N/D/H/Y |
| 10 | Y102 | YWC | F/Y/H/L |
| 11 | A104 | RST | S/T/A/G |
| 12 | V105 | NTC | F/I/L/V |
| 13 | L106 | NTT | F/I/L/V |
| 14 | Y107 | YWT | F/Y/H/L |
| 15 | E108 | RAW | E/D/K/N |

Theoretical diversity = $1.07 \times 10^9$
Actual diversity = $0.8 \times 10^8$ transformants

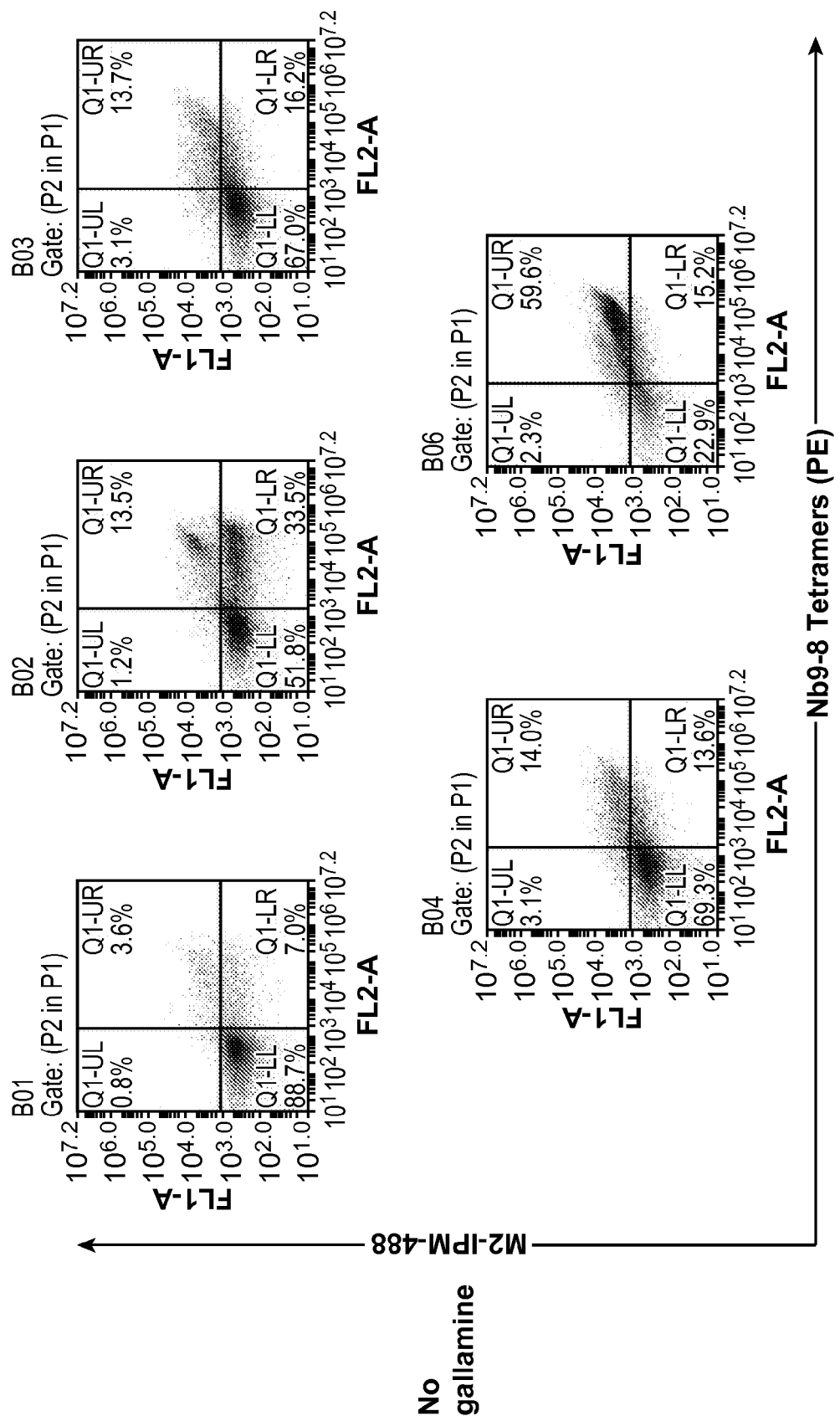
FIG. 13 (Cont. 1)

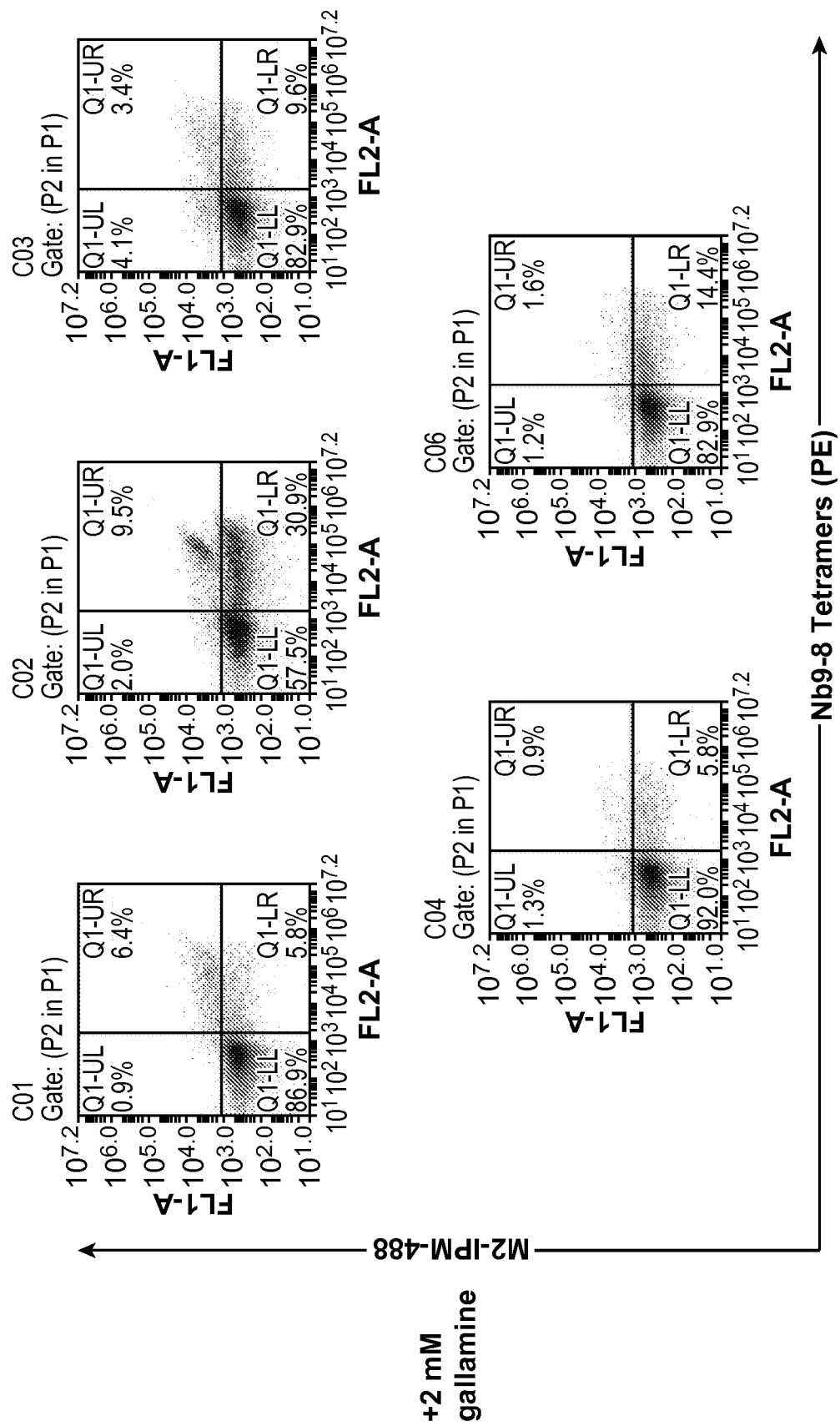
FIG. 13 (Cont. 2)

Alignment of M₂ extracellular nanobodies (post rd8):

```
Nb_C3:  QVC-QESGGGLVQPGGSLRLSCASGRSISNIYATTWYRQAPGKQRELVAVFGYSGGTTNYADSVKGRFTISRDAKNTVYLQMNIKPED?AVVCN----AVKY--IPGRGEYDYWGQGTQVTVSS
Nb_H4:  QVC-QESGGGLVQAGDSLRLSCAASAR-SFVSYAMGWFRQAPGKEREFVASISWSGTMTQYADSVKGRFTISRDDAKNTVYLQMNIKPED?AVVCN----AVKY--IPGRGEYDYWGQGTQVTVSS
Nb_E1:  QVC-QESGGGLVQAGGSLRLSCAASVR-TFSNYGMGWFRQGPGKEREFVASISWSGTMTQYADSVKGRFTISRDNAKSTVYLQMNIKPED?AVVCN----AVKY--IPGRGEYDYWGQGTQVTVSS
Nb_A2:  QVC-QESGGGLVQAGASINLSCAASGG-TFRHYGMGWFRQAPGKEREFVAAISWTGGVTFYGDSVKGRFTISRDEKNTVDLQMNNLKAED?AVVCN----VRGG-RPASRDDPGYWGQGTQVTVSS
Nb_B4:  QVC-QESGGGLVQAGGSLRLSCAASGR-TFSNYAMSWFRQAPGKERGLVATIYRSGEGTYLPSAKGRFTVSRDNAKNTAYLQMNSLKAED?AVVCA----VMS--RGTWSMWGQGTQVTVSS
Nb_D3:  QVC-QESGGGLVQAGGSLRLSCAASGF-SFDDYAICWFRQAPGKEREFVARINRSGYNTFYTDSVKGRFTISRDNAKNTVYLQMNSIKLED?AVVCCG----ARYSGSPFYSGADYWGQGTQVTVSS
Nb_D1:  QVC-QESGGGLVQPGGSLRLSCAASGS-IANLNSVGWYRQAPGKEREWVAAILAGG-FATYADSVKGRFTISRDAKNTVYLQMNSIKLED?AVVCNTPDR---------PGASWGQGTQVTVSS
Nb_H1:  QVC-QESGGGLVESGSLRLSCAASGF-TADDYTMSWVRQAPGKGLEWVSTIAASSVITFYADSVEGRFTISRDNAENIVYLQMNGLKPED?AVVCN----TYPPLWGRTPDEDYWGQGTQVTVSS
```

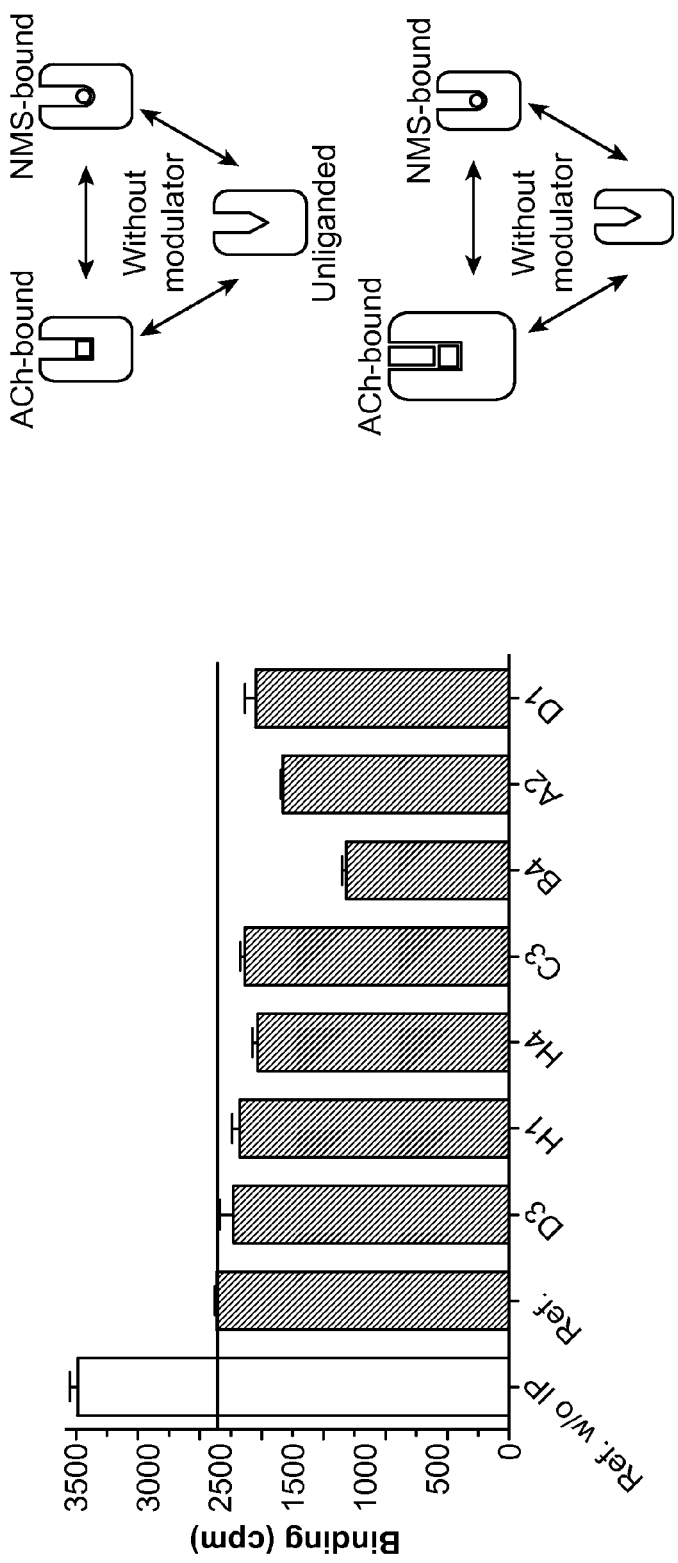

FIG. 14

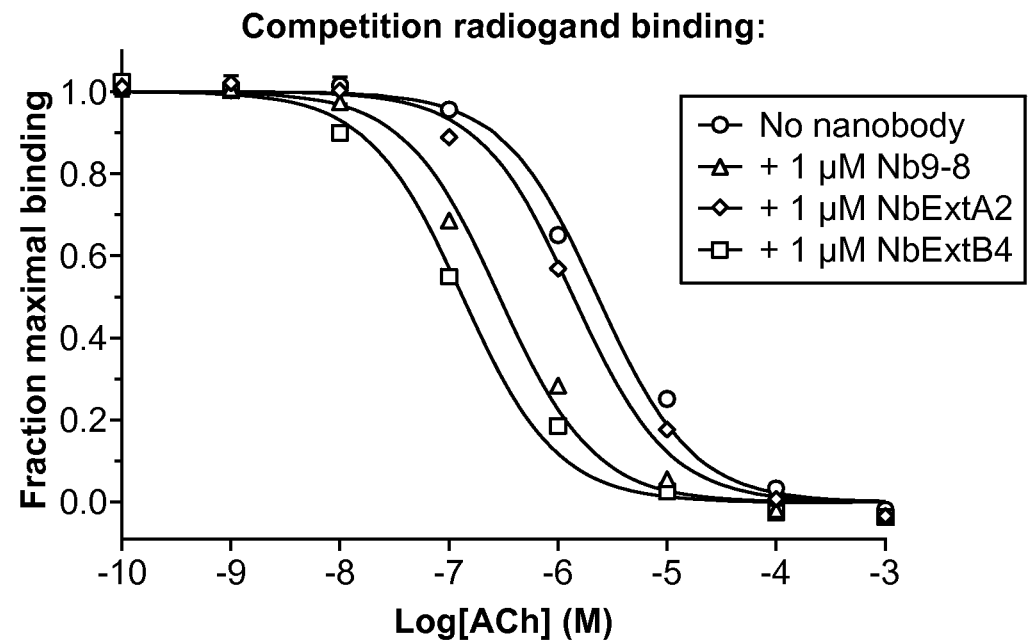
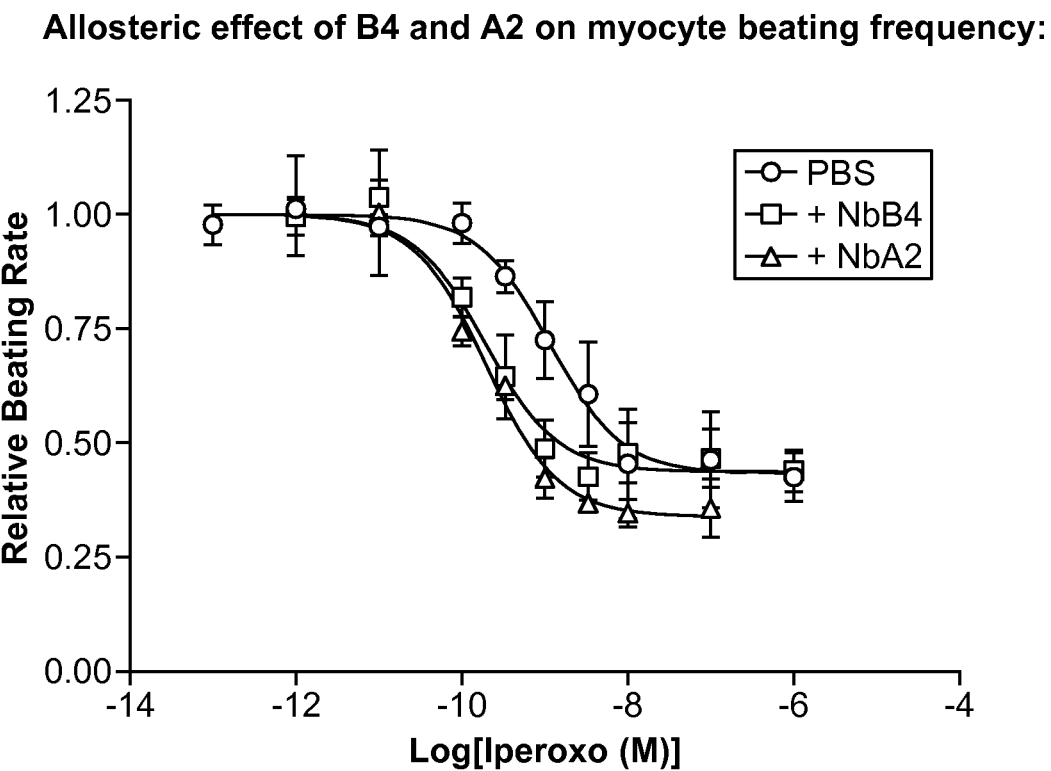
FIG. 15

SEQUENCE LISTING

```
<160> NUMBER OF SEQ ID NOS: 32

<210> SEQ ID NO 1
<211> LENGTH: 44
<212> TYPE: DNA
<213> ORGANISM: Artificial Sequence
<220> FEATURE:
<223> OTHER INFORMATION: synthetic polynucleotide

<400> SEQUENCE: 1
atggcccagg tgcagctgca ggagtctggg ggaggcttgg tgca                    44
```

<210> SEQ ID NO 2
<211> LENGTH: 53
<212> TYPE: DNA
<213> ORGANISM: Artificial sequence
<220> FEATURE:
<223> OTHER INFORMATION: synthetic polynucleotide

<400> SEQUENCE: 2
agaggctgca caggagagtc tcagagaccc cccagcctgc accaagcctc ccc    53

<210> SEQ ID NO 3
<211> LENGTH: 61
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (34)..(34)
<223> OTHER INFORMATION: n is a, c, g, or t

<400> SEQUENCE: 3
ctctcctgtg cagcctctgg arscatcywc rstntcaatr ycatgggctg gtaccgccag    60
g    61

<210> SEQ ID NO 4
<211> LENGTH: 47
<212> TYPE: DNA
<213> ORGANISM: Artificial sequence
<220> FEATURE:
<223> OTHER INFORMATION: synthetic polynucleotide

<400> SEQUENCE: 4
cgaccaactc gcgctgcttc cctggagcct ggcggtacca gcccatg    47

<210> SEQ ID NO 5
<211> LENGTH: 64
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (44)..(44)
<223> OTHER INFORMATION: n is a, c, g, or t

<400> SEQUENCE: 5
gcagcgcgag ttggtcgcar ytattywtag tggtggtwmc acanactatg ccaactccgt    60
gaag    64

<210> SEQ ID NO 6
<211> LENGTH: 49
<212> TYPE: DNA
<213> ORGANISM: Artificial sequence
<220> FEATURE:
<223> OTHER INFORMATION: synthetic polynucleotide

<400> SEQUENCE: 6
gcattgtctc tggagatggt gaatcggccc ttcacggagt tggcatagt    49

<210> SEQ ID NO 7
<211> LENGTH: 59
<212> TYPE: DNA
<213> ORGANISM: Artificial sequence
<220> FEATURE:
<223> OTHER INFORMATION: synthetic polynucleotide

<400> SEQUENCE: 7
caccatctcc agagacaatg ccgcgaacac ggtgtatctg caaatgaaca gcctgaaac    59

<210> SEQ ID NO 8
<211> LENGTH: 61
<212> TYPE: DNA
<213> ORGANISM: Artificial sequence
<220> FEATURE:
<223> OTHER INFORMATION: synthetic polynucleotide

<400> SEQUENCE: 8
cctttacatt acagtaatag acggccgtgt cctcaggttt caggctgttc atttgcagat    60
a                                                                   61

<210> SEQ ID NO 9
<211> LENGTH: 66
<212> TYPE: DNA
<213> ORGANISM: Artificial sequence
<220> FEATURE:
<223> OTHER INFORMATION: synthetic polynucleotide
<220> FEATURE:
<221> NAME/KEY: misc_feature
<222> LOCATION: (37)..(37)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t

<400> SEQUENCE: 9
gccgtctatt actgtaatgt aaaggacywc gggrstntcn ttywtrawta tgactactgg    60
ggccag                                                              66

<210> SEQ ID NO 10
<211> LENGTH: 42
<212> TYPE: DNA
<213> ORGANISM: Artificial sequence
<220> FEATURE:
<223> OTHER INFORMATION: synthetic polynucleotide

<400> SEQUENCE: 10
tgaggagacg gtgacctggg tcccctggcc ccagtagtca ta                      42

<210> SEQ ID NO 11
<211> LENGTH: 92
<212> TYPE: DNA
<213> ORGANISM: Artificial sequence
<220> FEATURE:
<223> OTHER INFORMATION: synthetic polynucleotide

<400> SEQUENCE: 11
cattttcaat taagatgcag ttacttcgct gttttcaat attttctgtt attgctagcg    60
ttttagcaat ggcccaggtg cagctgcagg ag                                 92

<210> SEQ ID NO 12
<211> LENGTH: 80
<212> TYPE: DNA
<213> ORGANISM: Artificial sequence
<220> FEATURE:
<223> OTHER INFORMATION: synthetic polynucleotide

<400> SEQUENCE: 12
ccaccagatc caccaccacc caagtcttct tcggagataa gcttttgttc ggatcctgag    60
gagacggtga cctgggtccc                                          80

<210> SEQ ID NO 13
<211> LENGTH: 122
<212> TYPE: PRT
<213> ORGANISM: Artificial sequence
<220> FEATURE:
<223> OTHER INFORMATION: synthetic polypeptide

<400> SEQUENCE: 13

Gln Val Gln Leu Gln Glu Ser Gly Gly Gly Leu Val Gln Ala Gly Gly
1               5                   10                  15

Ser Leu Arg Leu Ser Cys Ala Phe Ser Gly Arg Thr Phe Ser Asn Tyr
            20                  25                  30

Gly Met Gly Trp Phe Arg Gln Gly Pro Gly Lys Glu Arg Glu Phe Val
        35                  40                  45

Ala Ser Ile Ser Trp Ser Gly Thr Met Thr Gln Tyr Ala Asp Ser Val
    50                  55                  60

Lys Gly Arg Phe Thr Ile Ser Arg Asp Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Ala Lys Tyr Phe Val Ser Trp Tyr Pro Glu Gly Ala Leu Gly Ser Trp
            100                 105                 110

Gly Gln Gly Thr Gln Val Thr Val Ser Ser
        115                 120

<210> SEQ ID NO 14
<211> LENGTH: 122
<212> TYPE: PRT
<213> ORGANISM: Artificial sequence
<220> FEATURE:
<223> OTHER INFORMATION: synthetic polypeptide

<400> SEQUENCE: 14

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Gly Met Gly Trp Phe Arg Gln Gly Pro Gly Lys Glu Arg Glu Phe Val
        35                  40                  45

Ala Gly Ile Ser Trp Ser Gly Arg Ser Thr Tyr Tyr Ser Asp Ser Val
    50                  55                  60

Lys Gly Arg Phe Thr Ile Ser Arg Asp Asn Ala Lys His Thr Met Tyr
65                  70                  75                  80

Leu Gln Met Asn Ser Leu Lys Pro Glu Asp Thr Ala Val Tyr Tyr Cys
                85                  90                  95

Thr Ala Lys Thr Tyr Gly Ala Ala Arg Asp Pro Val Tyr Asp Tyr Trp
            100                 105                 110

Gly Pro Gly Thr Gln Val Thr Val Ser Ser
        115                 120

<210> SEQ ID NO 15
<211> LENGTH: 123
<212> TYPE: PRT
<213> ORGANISM: Artificial sequence
<220> FEATURE:
<223> OTHER INFORMATION: synthetic polypeptide

<400> SEQUENCE: 15

-continued

```
Gln Val Gln Leu Gln Glu Ser Gly Gly Gly Leu Val Gln Ala Gly Gly
1               5                   10                  15

Ser Leu Arg Leu Ser Cys Val Ala Ser Val Arg Thr Phe Ser Thr Tyr
            20                  25                  30

Ser Met Gly Trp Phe Arg Gln Ala Pro Gly Lys Glu Arg Glu Phe Leu
        35                  40                  45

Ala Gly Ile Ser Gly Ser Gly Asp Arg Thr Trp Tyr Arg Thr Ser Val
    50                  55                  60

Lys Gly Arg Phe Ala Ile Ser Arg Asp Asn Gly Lys Asn Thr Ala Tyr
65                  70                  75                  80

Leu Gln Met Asn Ser Leu Glu Pro Glu Asp Thr Ala Val Tyr Tyr Cys
                85                  90                  95

Ala Ala Arg Ser Pro Lys Cys His Ser Arg Ser Thr Tyr Tyr Asp Tyr
            100                 105                 110

Trp Gly Gln Gly Thr Gln Val Thr Val Ser Ser
        115                 120
```

<210> SEQ ID NO 16
<211> LENGTH: 118
<212> TYPE: PRT
<213> ORGANISM: Artificial sequence
<220> FEATURE:
<223> OTHER INFORMATION: synthetic polypeptide

<400> SEQUENCE: 16

```
Gln Val Gln Leu Gln Glu Ser Gly Gly Gly Leu Val His Ala Gly Gly
1               5                   10                  15

Ser Leu Arg Leu Ser Cys Thr Ala Ser Gly Arg Thr Ser Ser Arg Gly
            20                  25                  30

Gly Met Gly Trp Phe Arg Gln Ala Pro Gly Lys Asp Arg Glu Phe Val
        35                  40                  45

Ala Ala Ile Thr Trp Asn Ile Gly Ile Thr Tyr Tyr Glu Asp Ser Val
    50                  55                  60

Lys Gly Arg Phe Thr Val Ser Arg Asp Asn Ala Lys Asn Thr Leu Tyr
65                  70                  75                  80

Leu Gln Met Asn Ser Leu Lys Pro Glu Asp Thr Ala Val Tyr Tyr Cys
                85                  90                  95

Tyr Gly Gly Gly Gly Tyr Tyr Gly Gln Asp Ser Trp Gly Gln Gly Thr
            100                 105                 110

Gln Val Thr Val Ser Ser
        115
```

<210> SEQ ID NO 17
<211> LENGTH: 118
<212> TYPE: PRT
<213> ORGANISM: Artificial sequence
<220> FEATURE:
<223> OTHER INFORMATION: synthetic polypeptide

<400> SEQUENCE: 17

```
Gln Val Gln Leu Gln Glu Ser Gly Gly Gly Leu Val Gln Ala Gly Gly
1               5                   10                  15

Ser Leu Arg Leu Ser Cys Thr Ala Ser Gly Arg Thr Ser Ser Arg Gly
            20                  25                  30

Gly Met Ser Trp Phe Arg Gln Ala Pro Gly Lys Asp Arg Glu Phe Val
        35                  40                  45

Ala Ala Ile Ser Trp Asn Ile Gly Ile Thr Tyr Tyr Gly Asp Ser Val
```

```
                50              55                  60
Lys Gly Arg Phe Thr Val Ser Arg Asp Asn Ala Lys Asn Thr Val Tyr
 65              70                  75                  80

Leu Gln Met Asn Ser Leu Lys Pro Glu Asp Thr Ala Leu Tyr Tyr Cys
                 85                  90                  95

Ala Ala Gly Pro Arg Tyr Glu Asn Pro His Tyr Trp Gly Gln Gly Thr
                100                 105                 110

Gln Val Thr Val Ser Ser
                115
```

<210> SEQ ID NO 18
<211> LENGTH: 122
<212> TYPE: PRT
<213> ORGANISM: Artificial sequence
<220> FEATURE:
<223> OTHER INFORMATION: synthetic polypeptide

<400> SEQUENCE: 18

```
Gln Val Gln Leu Gln Glu Ser Gly Gly Gly Leu Val Gln Ala Gly Gly
 1               5                  10                  15

Ser Leu Arg Leu Ser Cys Ala Ala Ser Arg Arg Thr Gly Asn Met Tyr
                20                  25                  30

Asn Met Ala Trp Phe Arg Gln Ala Pro Gly Lys Glu Arg Glu Phe Val
             35                  40                  45

Ala Ala Ile Asn Trp Ser Gly Lys Asn Thr Tyr Tyr Ala Asp Ser Val
         50                  55                  60

Lys Gly Arg Phe Thr Ile Ser Arg Asp Asn Ala Lys Thr Thr Val Tyr
 65              70                  75                  80

Leu Glu Met Asn Ser Leu Lys Pro Glu Asp Thr Ala Val Tyr Tyr Cys
                 85                  90                  95

Ala Ala Gly Gly Cys Val Val Lys Ala Arg Asn Glu Cys Asp Phe Trp
                100                 105                 110

Gly Gln Gly Thr Gln Val Thr Val Ser Ser
                115                 120
```

<210> SEQ ID NO 19
<211> LENGTH: 124
<212> TYPE: PRT
<213> ORGANISM: Artificial sequence
<220> FEATURE:
<223> OTHER INFORMATION: synthetic polypeptide

<400> SEQUENCE: 19

```
Gln Val Gln Leu Gln Glu Ser Gly Gly Gly Leu Val Gln Ala Gly Ala
 1               5                  10                  15

Ser Leu Arg Leu Ser Cys Ala Ala Ser Gly Leu Thr Phe His Asp Tyr
                20                  25                  30

Asn Met Gly Trp Phe Arg Gln Ala Pro Gly Lys Glu Arg Glu Ser Val
             35                  40                  45

Ala Ala Ile Ser Arg Ser Gly Phe His Thr Tyr Tyr Ala Asp Ser Val
         50                  55                  60

Lys Gly Arg Phe Thr Ile Ser Arg Asp Asn Ser Lys Asn Thr Met Tyr
 65              70                  75                  80

Leu Gln Met Asn Ser Leu Lys Pro Glu Asp Thr Ala Val Tyr Tyr Cys
                 85                  90                  95

Ala Ala Arg Ser Thr Tyr Asn Ser Gly Arg Tyr Ser Glu Tyr Asp
                100                 105                 110
```

<210> SEQ ID NO 20
<211> LENGTH: 121
<212> TYPE: PRT
<213> ORGANISM: Artificial sequence
<220> FEATURE:
<223> OTHER INFORMATION: synthetic polypeptide

<400> SEQUENCE: 20

```
Gln Val Gln Leu Gln Glu Ser Gly Gly Gly Leu Val Gln Ala Gly Gly
1               5                   10                  15

Ser Leu Arg Leu Ser Cys Ala Ala Ser Gly His Thr Phe Ser Ser Ala
            20                  25                  30

Arg Met Tyr Trp Val Arg Gln Ala Pro Gly Lys Glu Arg Glu Phe Val
        35                  40                  45

Ala Ala Ile Ser Arg Ser Gly Phe Thr Tyr Ser Ala Asp Ser Val Lys
    50                  55                  60

Gly Arg Phe Thr Ile Ser Arg Asp Ile Ala Asn Asn Thr Val Tyr Leu
65                  70                  75                  80

Gln Met Asn Ser Leu Gln Pro Glu Asp Thr Ala Ile Tyr Thr Cys Tyr
                85                  90                  95

Ala Ala Tyr Leu Asp Glu Phe Tyr Asn Asp Tyr Thr His Tyr Trp Gly
            100                 105                 110

Leu Gly Thr Gln Val Thr Val Ser Ser
        115                 120
```

<210> SEQ ID NO 21
<211> LENGTH: 121
<212> TYPE: PRT
<213> ORGANISM: Artificial sequence
<220> FEATURE:
<223> OTHER INFORMATION: synthetic polypeptide

<400> SEQUENCE: 21

```
Gln Val Gln Leu Gln Glu Ser Gly Gly Gly Leu Val Gln Ala Gly Gly
1               5                   10                  15

Ser Leu Arg Leu Phe Cys Ala Ala Ser Gly Arg Thr Phe Ser Asn Tyr
            20                  25                  30

Asn Met Gly Trp Phe Arg Leu Ala Pro Gly Lys Glu Arg Glu Phe Val
        35                  40                  45

Ala Ala Ile Ser Arg Ser Ala Gly Ser Thr Ser Tyr Ala Asp Ser Val
    50                  55                  60

Lys Gly Arg Phe Thr Ile Ser Arg Asp Asn Thr Asn Asn Ile Val Tyr
65                  70                  75                  80

Leu Gln Met Asn Ser Val Glu Pro Glu Asp Thr Ala Val Tyr Tyr Cys
                85                  90                  95

Ala Lys Tyr Thr Arg Thr Tyr Pro Tyr Tyr Gly Met Asn Tyr Trp Gly
            100                 105                 110

Lys Gly Thr Gln Val Thr Val Ser Ser
        115                 120
```

<210> SEQ ID NO 22
<211> LENGTH: 121
<212> TYPE: PRT
<213> ORGANISM: Artificial sequence
<220> FEATURE:
<223> OTHER INFORMATION: synthetic polypeptide

```
<400> SEQUENCE: 22

Gln Val Gln Leu Gln Glu Ser Gly Gly Gly Leu Val Gln Ala Gly Asp
1               5                   10                  15

Ser Leu Arg Leu Ser Cys Ala Ala Ser Gly Phe Asp Phe Asp Asn Phe
            20                  25                  30

Asp Asp Tyr Ala Ile Gly Trp Phe Arg Gln Ala Pro Gly Gln Glu Arg
        35                  40                  45

Glu Gly Val Ser Cys Ile Asp Pro Ser Asp Gly Ser Thr Ile Tyr Ala
    50                  55                  60

Asp Ser Ala Lys Gly Arg Phe Thr Ile Ser Ser Asp Asn Ala Glu Asn
65                  70                  75                  80

Thr Val Tyr Leu Gln Met Asn Ser Leu Lys Pro Glu Asp Thr Ala Val
                85                  90                  95

Tyr Val Cys Ser Ala Trp Thr Leu Phe His Ser Asp Glu Tyr Trp Gly
            100                 105                 110

Gln Gly Thr Gln Val Thr Val Ser Ser
        115                 120

<210> SEQ ID NO 23
<211> LENGTH: 122
<212> TYPE: PRT
<213> ORGANISM: Artificial sequence
<220> FEATURE:
<223> OTHER INFORMATION: synthetic polypeptide

<400> SEQUENCE: 23

Gln Val Gln Leu Gln Glu Ser Gly Gly Gly Leu Val Gln Pro Glu Gly
1               5                   10                  15

Ser Leu Thr Leu Ala Cys Asp Thr Ser Gly Phe Thr Met Asn Tyr Tyr
            20                  25                  30

Ala Ile Ala Trp Phe Arg Gln Ala Pro Glu Lys Glu Arg Glu Gly Leu
        35                  40                  45

Ala Thr Ile Ser Ser Ile Asp Gly Arg Thr Tyr Tyr Ala Asp Ser Val
    50                  55                  60

Lys Gly Arg Phe Thr Ile Ser Arg Asp Ser Ala Lys Asn Met Val Tyr
65                  70                  75                  80

Leu Gln Met Asn Asn Leu Arg Pro Glu Asp Thr Ala Val Tyr Tyr Cys
                85                  90                  95

Ser Ala Gly Pro Asp Tyr Ser Asp Tyr Gly Asp Glu Ser Glu Tyr Trp
            100                 105                 110

Gly Gln Gly Thr Gln Val Thr Val Ser Ser
        115                 120

<210> SEQ ID NO 24
<211> LENGTH: 122
<212> TYPE: PRT
<213> ORGANISM: Artificial sequence
<220> FEATURE:
<223> OTHER INFORMATION: synthetic polypeptide

<400> SEQUENCE: 24

Gln Val Gln Leu Gln Glu Ser Gly Gly Gly Leu Val Gln Pro Gly Gly
1               5                   10                  15

Ser Leu Arg Leu Ser Cys Thr Ala Ser Gly Arg Ser Ile Ser Asn Ile
            20                  25                  30

Tyr Ala Thr Thr Trp Tyr Arg Gln Ala Pro Gly Lys Gln Arg Glu Leu
        35                  40                  45
```

Val Ala Val Phe Gly Tyr Ser Gly Gly Thr Thr Asn Tyr Ala Asp Ser
            50                  55                  60

Val Lys Gly Arg Phe Thr Ile Ser Arg Asp Asp Ala Lys Asn Thr Val
 65                  70                  75                  80

Tyr Leu Gln Met Asn Asn Leu Lys Pro Glu Asp Thr Ala Val Tyr Tyr
                85                  90                  95

Cys Asn Ala Val Lys Tyr Ile Pro Gly Arg Gly Glu Tyr Asp Tyr Trp
                100                 105                 110

Gly Gln Gly Thr Gln Val Thr Val Ser Ser
            115                 120

<210> SEQ ID NO 25
<211> LENGTH: 121
<212> TYPE: PRT
<213> ORGANISM: Artificial sequence
<220> FEATURE:
<223> OTHER INFORMATION: synthetic polypeptide

<400> SEQUENCE: 25

Gln Val Gln Leu Gln Glu Ser Gly Gly Gly Ala Val Gln Ala Gly Asp
 1               5                   10                  15

Ser Leu Arg Leu Ser Cys Ala Ser Ala Arg Ser Phe Val Ser Tyr
            20                  25                  30

Ala Met Gly Trp Phe Arg Gln Ala Pro Gly Lys Glu Arg Glu Phe Val
            35                  40                  45

Ala Ser Ile Ser Trp Ser Gly Thr Met Thr Gln Tyr Ala Asp Ser Val
            50                  55                  60

Lys Gly Arg Phe Thr Ile Ser Arg Asp Asp Ala Lys Asn Thr Val Tyr
 65                  70                  75                  80

Leu Gln Met Asn Asn Leu Lys Pro Glu Asp Thr Ala Val Tyr Tyr Cys
                85                  90                  95

Asn Ala Val Lys Tyr Ile Pro Gly Arg Gly Glu Tyr Asp Tyr Trp Gly
                100                 105                 110

Gln Gly Thr Gln Val Thr Val Ser Ser
            115                 120

<210> SEQ ID NO 26
<211> LENGTH: 121
<212> TYPE: PRT
<213> ORGANISM: Artificial sequence
<220> FEATURE:
<223> OTHER INFORMATION: synthetic polypeptide

<400> SEQUENCE: 26

Gln Val Gln Leu Gln Glu Ser Gly Gly Gly Leu Val Gln Ala Gly Gly
 1               5                   10                  15

Ser Leu Arg Leu Ser Cys Thr Ala Ser Val Arg Thr Phe Ser Asn Tyr
            20                  25                  30

Gly Met Gly Trp Phe Arg Gln Gly Pro Gly Lys Glu Arg Glu Phe Val
            35                  40                  45

Ala Ser Ile Ser Trp Ser Gly Thr Met Thr Gln Tyr Ala Asp Ser Val
            50                  55                  60

Lys Gly Arg Phe Thr Ile Ser Arg Asp Asn Ala Lys Ser Thr Val Tyr
 65                  70                  75                  80

Leu Gln Met Asn Asn Leu Lys Pro Glu Asp Thr Ala Val Tyr Tyr Cys
                85                  90                  95

Asn Ala Val Lys Tyr Ile Pro Gly Arg Gly Glu Tyr Asp Tyr Trp Gly
                100                 105                 110

Gln Gly Thr Gln Val Thr Val Ser Ser
        115                 120

<210> SEQ ID NO 27
<211> LENGTH: 122
<212> TYPE: PRT
<213> ORGANISM: Artificial sequence
<220> FEATURE:
<223> OTHER INFORMATION: synthetic polypeptide

<400> SEQUENCE: 27

Gln Val Gln Leu Gln Glu Ser Gly Gly Gly Leu Val Gln Ala Gly Ala
1               5                   10                  15

Ser Leu Asn Leu Ser Cys Ala Ala Ser Gly Gly Thr Phe Arg His Tyr
            20                  25                  30

Gly Met Gly Trp Phe Arg Gln Ala Pro Gly Lys Glu Arg Glu Phe Val
        35                  40                  45

Ala Ala Ile Ser Trp Thr Gly Gly Val Thr Phe Tyr Gly Asp Ser Val
    50                  55                  60

Lys Gly Arg Phe Thr Ile Ser Arg Asp Asp Glu Lys Asn Thr Val Asp
65                  70                  75                  80

Leu Gln Met Asn Asn Leu Lys Ala Glu Asp Thr Ala Val Tyr Tyr Cys
                85                  90                  95

Asn Val Arg Gly Gly Arg Pro Ala Ser Arg Asp Pro Gly Tyr Trp
            100                 105                 110

Gly Gln Gly Thr Gln Val Thr Val Ser Ser
        115                 120

<210> SEQ ID NO 28
<211> LENGTH: 117
<212> TYPE: PRT
<213> ORGANISM: Artificial sequence
<220> FEATURE:
<223> OTHER INFORMATION: synthetic polypeptide

<400> SEQUENCE: 28

Gln Val Gln Leu Gln Glu Ser Gly Gly Gly Leu Val Gln Ala Gly Gly
1               5                   10                  15

Ser Leu Arg Leu Ser Cys Ala Ala Ser Gly Arg Thr Phe Ser Asn Tyr
            20                  25                  30

Ala Met Ser Trp Phe Arg Gln Ala Pro Gly Lys Glu Arg Gly Leu Val
        35                  40                  45

Ala Thr Ile Tyr Arg Ser Gly Glu Gly Thr Tyr Tyr Leu Pro Ser Ala
    50                  55                  60

Lys Gly Arg Phe Thr Val Ser Arg Asp Asn Ala Lys Asn Thr Ala Tyr
65                  70                  75                  80

Leu Gln Met Asn Ser Leu Lys Ala Glu Asp Thr Ala Val Tyr Tyr Cys
                85                  90                  95

Ala Val Met Ser Arg Gly Thr Trp Ser Met Trp Gly Gln Gly Thr Gln
            100                 105                 110

Val Thr Val Ser Ser
        115

<210> SEQ ID NO 29
<211> LENGTH: 123
<212> TYPE: PRT
<213> ORGANISM: Artificial sequence
<220> FEATURE:
<223> OTHER INFORMATION: synthetic polypeptide

<400> SEQUENCE: 29

Gln Val Gln Leu Gln Glu Ser Gly Gly Gly Leu Val Gln Ala Gly Gly
1               5                   10                  15

Ser Leu Arg Leu Ser Cys Ala Ala Ser Gly Phe Ser Phe Asp Asp Tyr
            20                  25                  30

Ala Ile Gly Trp Phe Arg Gln Ala Pro Gly Lys Glu Arg Glu Phe Val
        35                  40                  45

Ala Arg Ile Asn Arg Ser Gly Tyr Asn Thr Phe Tyr Thr Asp Ser Val
    50                  55                  60

Lys Gly Arg Phe Thr Ile Ser Arg Glu Asn Ala Lys Asn Thr Val Tyr
65                  70                  75                  80

Leu Gln Met Asn Asn Leu Lys Pro Glu Asp Thr Ala Val Tyr Tyr Cys
                85                  90                  95

Gly Ala Arg Tyr Ser Gly Ser Pro Phe Tyr Ser Gly Ala Tyr Asp Tyr
            100                 105                 110

Trp Gly Gln Gly Thr Gln Val Thr Val Ser Ser
        115                 120

<210> SEQ ID NO 30
<211> LENGTH: 115
<212> TYPE: PRT
<213> ORGANISM: Artificial sequence
<220> FEATURE:
<223> OTHER INFORMATION: synthetic polypeptide

<400> SEQUENCE: 30

Gln Val Gln Leu Gln Glu Ser Gly Gly Gly Leu Val Gln Pro Gly Gly
1               5                   10                  15

Ser Leu Arg Leu Ser Cys Ala Ala Ser Gly Ser Ile Ala Asn Leu Asn
            20                  25                  30

Ser Val Gly Trp Tyr Arg Gln Ala Pro Gly Lys Glu Arg Glu Trp Val
        35                  40                  45

Ala Ala Ile Leu Ala Gly Gly Phe Ala Thr Tyr Ala Asp Ser Val Lys
    50                  55                  60

Gly Arg Phe Thr Ile Ser Arg Asp Asn Ala Lys Asn Thr Val Tyr Leu
65                  70                  75                  80

Gln Met Asn Ser Leu Lys Leu Glu Asp Thr Ala Val Tyr Tyr Cys Asn
                85                  90                  95

Thr Pro Asp Arg Pro Gly Ala Ser Trp Gly Gln Gly Thr Gln Val Thr
            100                 105                 110

Val Ser Ser
        115

<210> SEQ ID NO 31
<211> LENGTH: 122
<212> TYPE: PRT
<213> ORGANISM: Artificial sequence
<220> FEATURE:
<223> OTHER INFORMATION: synthetic polypeptide

<400> SEQUENCE: 31

Gln Val Gln Leu Gln Glu Ser Gly Gly Gly Leu Val Glu Ser Gly Gly
1               5                   10                  15

Ser Leu Arg Leu Ser Cys Ala Ala Ser Gly Phe Thr Ala Asp Asp Tyr
            20                  25                  30

Thr Met Ser Trp Val Arg Gln Ala Pro Gly Lys Gly Leu Glu Trp Val
        35                  40                  45

```
Ser Thr Ile Ala Ala Ser Ser Val Ile Thr Phe Tyr Ala Asp Ser Val
        50                  55                  60

Glu Gly Arg Phe Thr Ile Ser Arg Asp Asn Ala Glu Asn Ile Val Tyr
 65                  70                  75                  80

Leu Gln Met Asn Gly Leu Lys Pro Glu Asp Thr Ala Val Tyr Tyr Cys
                 85                  90                  95

Asn Thr Tyr Pro Pro Leu Trp Gly Arg Thr Pro Asp Glu Asp Tyr Trp
                100                 105                 110

Gly Gln Gly Thr Gln Val Thr Val Ser Ser
            115                 120

<210> SEQ ID NO 32
<211> LENGTH: 15
<212> TYPE: PRT
<213> ORGANISM: Artificial Sequence
<220> FEATURE:
<223> OTHER INFORMATION: synthetic polypeptide

<400> SEQUENCE: 32

Gly Leu Asn Asp Ile Phe Glu Ala Gln Lys Ile Glu Trp His Glu
 1               5                  10                  15
```

METHOD FOR SELECTING AGENTS THAT BIND TO TRANSMEMBRANE RECEPTORS IN A CONFORMATIONALLY SELECTIVE MANNER

CROSS-REFERENCING

This application is a § 371 application of PCT International Patent application serial no. US2014/014892, filed on Feb. 5, 2014, which claims the benefit of U.S. provisional application Ser. No. 61/761,136, filed on Feb. 5, 2013, which application is incorporated by reference herein.

GOVERNMENT RIGHTS

This invention was made with Government support under contracts DK094541 and NS028471 awarded by the National Institutes of Health. The Government has certain rights in the invention.

BACKGROUND

Many transmembrane receptors such as G protein-coupled receptors (GPCRs), transporters, and ion channels exist in many interconvertible three-dimensional conformations depending on their activity or ligand-binding state. Agents that specifically bind to a transmembrane receptor in a conformationally-specific way can be used to induce a conformational change in the transmembrane receptor. Such agents have therapeutic applications and can be used in X-ray crystallography studies of the transmembrane receptor.

SUMMARY

Provided herein are several methods for selecting agents that bind to transmembrane receptors in a conformationally-selective way. In some embodiments, the method may comprise: producing a transmembrane receptor in an active conformation; and the same transmembrane receptor in an inactive conformation; and using cell sorting to select, from a population of cells comprising a library of cell surface-tethered extracellular capture agents, cells that are specifically bound to either the transmembrane receptor in its active conformation or the transmembrane receptor in its inactive conformation, but not both. In other embodiments, the method may comprise: contacting a GPCR with a population of cells that comprise a library of surface-tethered extracellular proteins; labeling the cell population with a G-protein or mimetic thereof that specifically binds to the GPCR in its active or inactive state; and using cell sorting to select cells that bind to the G-protein or mimetic thereof. Also provided is a composition comprising a complex comprising: a GPCR and modulator of the GPCR, where the GPCR is maintained in an active or inactive conformation by the modulator; a detergent; cholesterol or an analog thereof; and a cell. This composition may be used in some of the screening methods described above.

BRIEF DESCRIPTION OF THE FIGURES

The skilled artisan will understand that the drawings, described below, are for illustration purposes only. The drawings are not intended to limit the scope of the present teachings in any way.

FIG. 5 shows analysis of test staining of $\beta_2$ adrenergic receptor binding to Nb80 yeast.

FIG. 14 summarizes sequences of selected functional, extracellular $M_2$ nanobody ligands and their effect on $M_2$ receptor in a radioligand binding assay (From top to bottom SEQ ID NOs:24-31).

FIG. 15 shows additional characterization of the allosteric effect of nanobodies NbB4 and NbA2 isolated using M2 receptor and Gi mimetic 9-8.

DEFINITIONS

Figure 1:
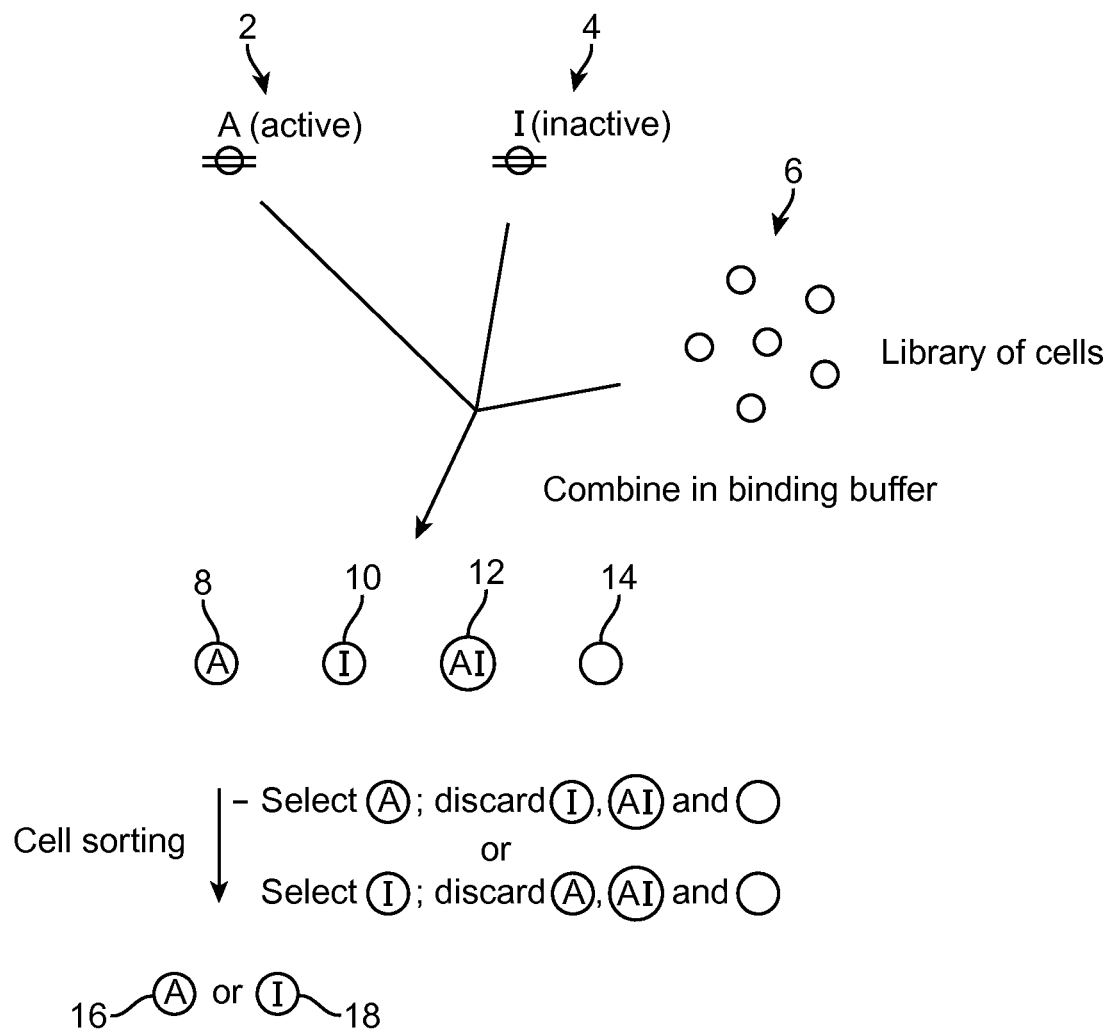
FIG. 1 schematically illustrates one way in which one embodiment of the method can be performed.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Marham, THE HARPER COLLINS DICTIONARY OF BIOLOGY, Harper Perennial, NY (1991) provide one of skill with general dictionaries of many of the terms used in this disclosure. Although any methods and materials similar or equivalent to those described herein can be used in the practice or testing of the present invention, the preferred methods and materials are described.

All patents and publications, including all sequences disclosed within such patents and publications, referred to herein are expressly incorporated by reference.

Numeric ranges are inclusive of the numbers defining the range. Unless otherwise indicated, nucleic acids are written left to right in 5' to 3' orientation; amino acid sequences are written left to right in amino to carboxy orientation, respectively.

The headings provided herein are not limitations of the various aspects or embodiments of the invention which can be had by reference to the specification as a whole. Accordingly, the terms defined immediately below are more fully defined by reference to the specification as a whole.

The term "transmembrane receptor" refers to any integral membrane protein whose activity can be modulated by ligand binding or a conformational change. G protein-coupled, ion channel-linked, enzyme-linked, carrier transport proteins, PAQR and sigma receptors are types of transmembrane receptor. G protein-coupled receptors (GP- CRs) possess seven transmembrane alpha helices as described in greater detail. When a GPCR is activated, the GPCR activates an associated G-protein that in turn activates intracellular signaling cascades. Ion channel-linked receptors (i.e., ligand gated ion channels) are also known as ionotropic receptors. Binding of a ligand to such an ion channel results in opening of the channel to increase ion flow through the channel or closing to decrease ion flow. Enzyme-linked receptors (also known as catalytic receptors) are receptors in which activation by binding of an extracellular ligand triggers enzymatic activity on the intracellular side of the protein. Carrier proteins couple the transport of ions, small molecules, and macromolecules across the cellular membrane to conformational changes in the receptor through passive, 'facilitated diffusion' or through active transport mechanisms requiring an electrochemical gradient or adenosine trisphosphate-dependent processes.

The term "naturally-occurring" in reference to a transmembrane receptor means a transmembrane receptor that is naturally produced (e.g., by a wild-type mammal such as a human). Such transmembrane receptors are found in nature. The term "non-naturally occurring" in reference to a transmembrane receptor means a transmembrane receptor that is not naturally-occurring. Naturally-occurring transmembrane receptors that have been made constitutively active through mutation, and variants of naturally-occurring transmembrane receptors, e.g., epitope-tagged transmembrane receptors and transmembrane receptors lacking their native N-terminus are examples of non-naturally occurring transmembrane receptors. Non-naturally occurring versions of a naturally occurring transmembrane receptor are often activated by the same ligand as the naturally-occurring transmembrane receptor.

"G-protein coupled receptors" or "GPCRs" are polypeptides that share a common structural motif, having seven regions of between 22 to 24 hydrophobic amino acids that form seven alpha helices, each of which spans a membrane. Each span is identified by number, i.e., transmembrane-1 (TM1), transmembrane-2 (TM2), etc. The transmembrane helices are joined by regions of amino acids between transmembrane-2 and transmembrane-3, transmembrane-4 and transmembrane-5, and transmembrane-6 and transmembrane-7 on the exterior, or "extracellular" side, of the cell membrane, referred to as "extracellular" regions 1, 2 and 3 (EC1, EC2 and EC3), respectively. The transmembrane helices are also joined by regions of amino acids between transmembrane-1 and transmembrane-2, transmembrane-3 and transmembrane-4, and transmembrane-5 and transmembrane-6 on the interior, or "intracellular" side, of the cell membrane, referred to as "intracellular" regions 1, 2 and 3 (IC1, IC2 and IC3), respectively. The "carboxy" ("C") terminus of the receptor lies in the intracellular space within the cell, and the "amino" ("N") terminus of the receptor lies in the extracellular space outside of the cell. GPCR structure and classification is generally well known in the art, and further discussion of GPCRs may be found in Probst, DNA Cell Biol. 1992 11:1-20; Marchese et al Genomics 23: 609-618, 1994; and the following books: Jürgen Wess (Ed) Structure-Function Analysis of G Protein-Coupled Receptors published by Wiley-Liss (1st edition; Oct. 15, 1999); Kevin R. Lynch (Ed) Identification and Expression of G Protein-Coupled Receptors published by John Wiley & Sons (March 1998) and Tatsuya Haga (Ed), G Protein-Coupled Receptors, published by CRC Press (Sep. 24, 1999); and Steve Watson (Ed) G-Protein Linked Receptor Factsbook, published by Academic Press (1st edition; 1994).

The term "ligand" means a molecule that specifically binds to a transmembrane receptor. A ligand may be, for example a polypeptide, a lipid, a small molecule, an antibody. A "native ligand" is a ligand that is an endogenous, natural ligand for a native transmembrane receptor. A ligand may be an "antagonist", "agonist", "partial agonist" or "inverse agonist", or the like.

A "modulator" is a ligand that increases or decreases an intracellular response when it is in contact with, e.g., binds to, a transmembrane receptor that is expressed by a cell. This term includes agonists, including partial agonists and inverse agonists, and antagonists.

The term "biologically active", with respect to a transmembrane receptor, refers to a transmembrane receptor having a biochemical function (e.g., a binding function, a signal transduction function, or an ability to change conformation as a result of ligand binding) of a naturally occurring transmembrane receptor.

The term "antibody" is intended to mean an immunoglobulin or any fragment thereof that is capable of antigen binding. The term "antibody" also refers to single chain antibodies and antibodies with only one binding domain.

As used herein, the terms "determining," "measuring," "assessing," and "assaying" are used interchangeably and include both quantitative and qualitative determinations. Reference to an "amount" of a GPCR in these contexts is not intended to require quantitative assessment, and may be either qualitative or quantitative, unless specifically indicated otherwise.

As used herein the term "isolated," when used in the context of an isolated compound, refers to a compound of interest that is in an environment different from that in which the compound naturally occurs. "Isolated" is meant to include compounds that are within samples that are substantially enriched for the compound of interest and/or in which the compound of interest is partially or substantially purified.

As used herein, the term "substantially pure" refers to a compound that is removed from its natural environment and is at least 60% free, at least 75% free, or at least 90% free from other components with which it is naturally associated.

The terms "active conformation" and "active form" refer to a transmembrane receptor that is folded in a way so as to be active. A transmembrane receptor can be placed into an active conformation using an agonist of the receptor. A GPCR in its active conformation binds to heterotrimeric G protein and catalyzes nucleotide exchange of the G-protein to activate downstream signaling pathways. Activated GPCRs bind to the inactive, GDP-bound form of heterotrimeric G-proteins and cause the G-proteins to release their GDP so GTP can bind. There is a transient 'nucleotide-free' state that results from this process that enables GTP to bind. Once GTP is bound, the receptor and G-protein dissociate, allowing the GTP-bound G-protein to activate downstream signaling pathways such as adenylyl cyclase, ion channels, RAS/MAPK, etc.

The terms "inactive conformation" and "inactive form" refer to a transmembrane receptor that is folded in a way so as to be inactive. A transmembrane receptor can be placed into an inactive conformation using an antagonist of the receptor. A GPCR in its inactive conformation does not bind to heterotrimeric G protein with high affinity.

As used herein, the term "cell sorting" refers to a method by which the individual cells of a sample are sorted by their optical (e.g., fluorescence etc.) or magnetic properties. Fluorescence activated cell sorting (FACS) and magnet activated cell sorting (MACS) are methods by which a population of cells having particular optical or magnetic properties are separated from other cells.

As used herein, the term "surface tethered" refers to a protein that is attached to the exterior surface of a cell such that the protein is exposed, i.e., displayed, on the outside of the cell.

The term "capture agent" refers to an agent that is composed of a single polypeptide chain that binds a target molecule through an interaction that is sufficient to permit the agent to bind and concentrate the target molecule from a heterogeneous mixture of different molecules. The binding interaction is typically mediated by an affinity region of the capture agent. Typical capture agents include any moiety that can specifically bind to a target molecule. Capture agents specifically bind a target molecule with a dissociation constant ($K_D$) of less than about $10^{-6}$ M (e.g., less than about $10^{-7}$M, less than about $10^{-8}$M, less than about $10^{-9}$M, less than about $10^{-10}$ M, less than about $10^{-11}$ M, less than about $10^{-12}$ M, to as low as $10^{-16}$ M) without significantly binding to other molecules. Exemplary capture agents include single chain antibodies and an alternative scaffold capture agent.

The terms "specific binding" and "selective binding" refer to the ability of a capture agent to preferentially bind to a particular target molecule that is present in a heterogeneous mixture of different target molecule. A specific or selective binding interaction will discriminate between desirable (e.g., active) and undesirable (e.g., inactive) target molecules in a sample, typically more than about 10 to 100-fold or more (e.g., more than about 1000- or 10,000-fold).

For the purposes of this disclosure, a "single chain antibody" is an antibody that contains an antigen binding site that is composed of a single polypeptide chain. One example of a single chain antibody is a single-chain variable fragment (scFv) antibody, which is a fusion protein that contains the variable regions of the heavy (VH) and light chains (VL) of a classical antibody connected by a short linker peptide of about ten to about 25 amino acids. A single-chain antibody can also be obtained by immunization of a camelid (e.g., a camel, llama or alpaca) or a cartilaginous fish (e.g., a shark), which make antibodies that are composed of only heavy chains. A monomeric variable domain of a heavy chain antibody binds antigen.

The term "alternative scaffold capture agent" refers to any monomeric protein (i.e., a protein that is composed of a single chain of amino acids that is encoded by a single gene) that has a target binding domain and that can autonomously (i.e., without additional polypeptides) bind to a target. Like an antibody, an alternative scaffold capture agent contains a "framework", which is largely structural, and a "binding domain" which makes contact with the target and provides for specific binding. The binding domain of an alternative scaffold capture agent need not be defined by one contiguous sequence. In certain cases, an alternative scaffold capture agent may be part of larger binding protein, which, itself, may be part of a multimeric binding protein that contains multiple scaffolds. An alternative scaffold capture agent may be derived from (i.e., have the same structure as but not necessarily the same amino acid sequence as) a single chain antibody (as defined above), or an alternative scaffold capture agent may be not antibody-derived, in which a case it may have no sequence or structural relation to an antibody variable domain. Fibronectin type III domains (FN3's), adnectins, DARPins, affibodies, avian pancreatic peptides (APPs), lipocalins, atrimers, kringle domains, phylomers and centyrins, etc. are examples of alternative scaffolds that can be employed in an alternative scaffolds capture agents. Ligand based scaffolds may be used for those receptors whose ligands are proteins.

The term "distinguishably tagged" refers to a modification that allows two proteins (which may be otherwise identical to one another) to be distinguished from one another. Two proteins can be distinguishably tagged using two different epitope tags (which allow the proteins to be separately identified using labeled antibodies that bind to those tags), or using two fluorescent labels, for example.

The term "a population of cells that comprise a library of surface-tethered extracellular capture agents" refers to a population of that cells that expresses (i.e., "displays") a surface-tethered capture agent on their exterior surface and the amino acid sequence of the capture agent differs from cell to cell.

As used herein, the term "biotin moiety" refers to an affinity agent that includes biotin or a biotin analogue such as desthiobiotin, oxybiotin, 2'-iminobiotin, diaminobiotin, biotin sulfoxide, biocytin, etc. Biotin moieties bind to streptavidin with an affinity of at least $10^{-8}$ M. A biotin affinity agent may also include a linker, e.g., -LC-biotin, -LC-LC-Biotin, -SLC-Biotin or -PEG$_n$-Biotin where n is 3-12.

Other definitions may be found in the detailed description.

DETAILED DESCRIPTION OF EXEMPLARY EMBODIMENTS

As noted above, this disclosure provides a selection method that can be used to isolate agents that bind to a transmembrane receptor in a conformationally selective way. In general terms, the method involves producing an active form of a transmembrane receptor (i.e., a transmembrane receptor that is in its active conformation) and an inactive form of the transmembrane receptor (i.e., a transmembrane receptor that is in its inactive conformation) in separate vessels, where the active and inactive forms of the receptors should be otherwise identical in amino acid sequence except for any distinguishable tags (e.g., epitope tags) that are added to the sequences.

The inactive and active forms of the receptors may be made by expressing the receptor in a host cell (e.g., using baculovirus expression in insect cells), solubilizing the receptor using a detergent, and purifying the receptor (e.g., by affinity chromatography using a purification tag that has been added to the receptor). Methods for purifying such membrane receptors are known in the art (see, e.g., Kobilka et al, Analytical Biochemistry 1995 231, 269-271, among many others). The active and inactive forms of the receptor can be produced by incubating one sample (e.g., a first aliquot) of purified receptor with an agonist (to produce the active form of the receptor) and, separately, incubating another sample (e.g., a second aliquot) of purified receptor with an antagonist (to produce the inactive form of the receptor). The identity of the agonist or antagonist used to induce the membrane proteins in the active and inactive conformations can vary greatly depending on the membrane receptor used, many examples of suitable agonists or antagonists are known in the art. Further, suitable agonists and antagonists are relatively straightforward to identify. Suitable agonists and antagonists may have a $K_d$ of less than $10^{-5}$, e.g., less than $10^{-6}$, less than $10^{-7}$, less than $10^{-8}$ or less than $10^{-9}$, with a dissociation half-life of at least 1 hr (e.g., at least 5 hours, at least 10 hours, or at least 20 hours) thereby ensuring that receptor should be populated in its active or inactive conformation during future steps. If a ligand has a lower off-rate (e.g., a dissociation half-life of less than 1 hr), then the ligand can be used at a higher concentration (e.g., a saturating concentration). The active form of a receptor may also be induced by a physiological stimulus, e.g., a low pH, or using a thermostabilizing mutation (see. e.g., J Mol Biol. 2011 409:298-310). In certain cases, the receptor may be covalently bound to the agonist or antagonist, as described in Rosenbaum et al (Nature 2011 469: 236-240), or the receptor may be thermostabilized prior to binding to agonist or antagonist, as described in Warne et al (Nature 2011 469: 241-244). In particular embodiments, the native ligand of the membrane protein, or an analog thereof, may be used to place the GPCR in its active conformation.

Depending on the exact way in which the screening method is implemented, the active and inactive forms of the receptors can be distinguishably tagged (e.g., using epitope tags or by conjugating those molecules to distinguishable fluorophores) so that they can be separately detected in the same vessel. In these embodiments, the inactive and active forms of the receptor may be tagged with a binding agent (e.g., a biotin moiety), and then the inactive form may be bound to a first fluorophore conjugated to streptavidin and, separately, the active form may be bound to a second fluorophore (distinguishable from the first fluorophore) conjugated to streptavidin. In other embodiments, the receptors may be tagged with the same fluorescent or magnetic tag (e.g., via a biotin moiety that has been added to the receptor). In these embodiments, the active and inactive receptors can be separately identified, but not in the same vessel. In certain embodiments, a transmembrane receptor may be labeled via an exposed cysteine residue (which can be reacted with a maleimide or iodoacetamide that is conjugated to a biotin moiety or a fluorophore) or an exposed lysine residue (which can be reacted with an active ester, such as a succinimidyl ester, or an isothiocyanate that is conjugated to a biotin moiety or a fluorophore), using an epitope tag (e.g., the V5, FLAG, HA, myc, rhodopsin 1D4, polyhistidine, VSV-G, or HSV tag) or by making the transmembrane protein in the form of a micelle that contains a fluorophore within the micelle.

The inactive and active forms of the receptor are then employed in a cell sorting protocol (e.g., FACS or MACS) to select, from a population of cells comprising a library of cell surface-tethered extracellular capture agents (e.g., surface-tethered single chain antibodies or alternative scaffold proteins), cells that are selectively bound to either the transmembrane receptor in its active conformation or the transmembrane receptor in its inactive conformation, but not both (i.e., not both the inactive and active forms of the receptor). As would be recognized, if epitope tags and antibodies are used, then the antibodies may be added after the transmembrane proteins have been bound to the cells.

Figure 2:
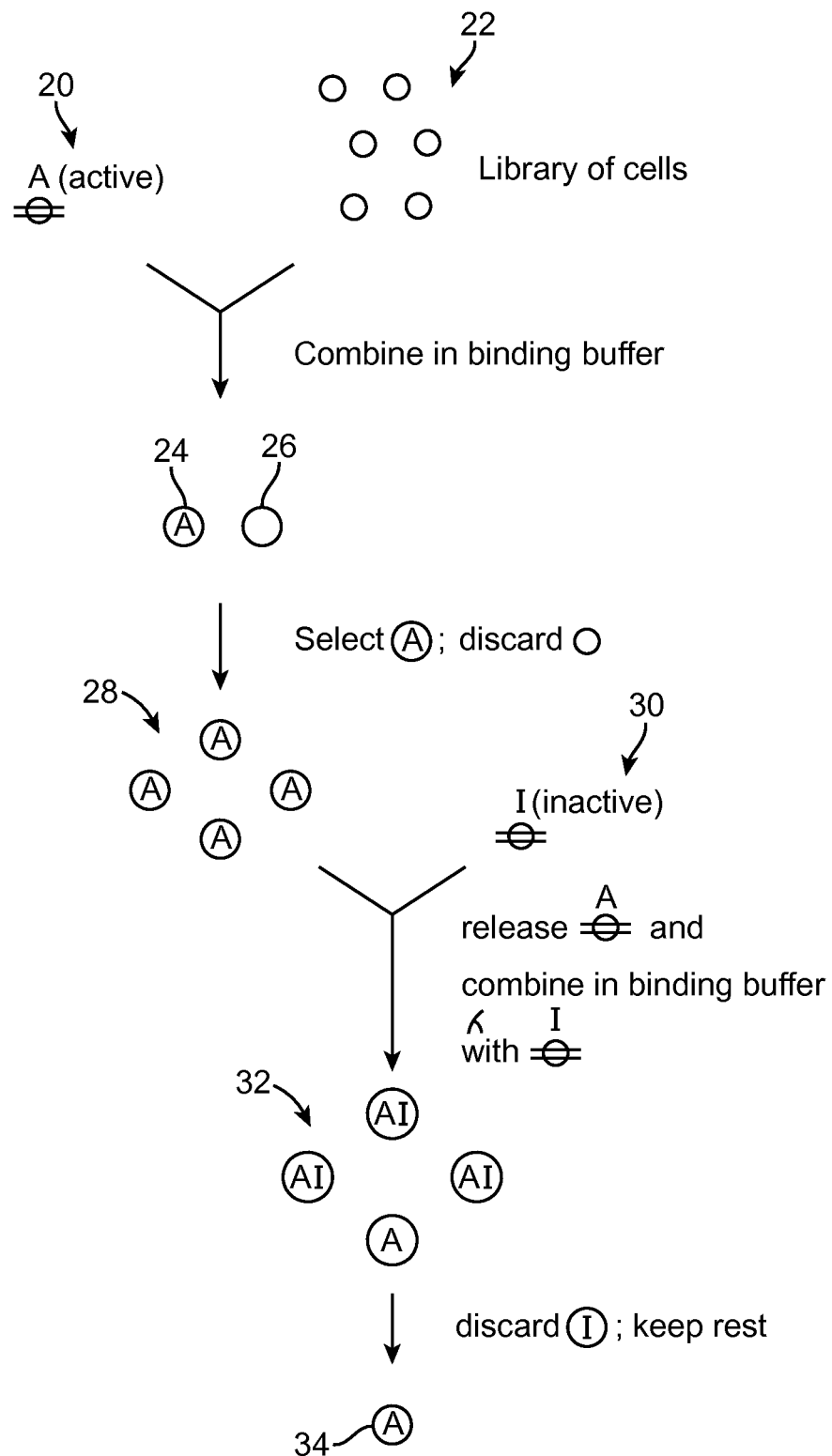
FIG. 2 schematically illustrates another way in which one embodiment of the method can be performed.
Figure 3:
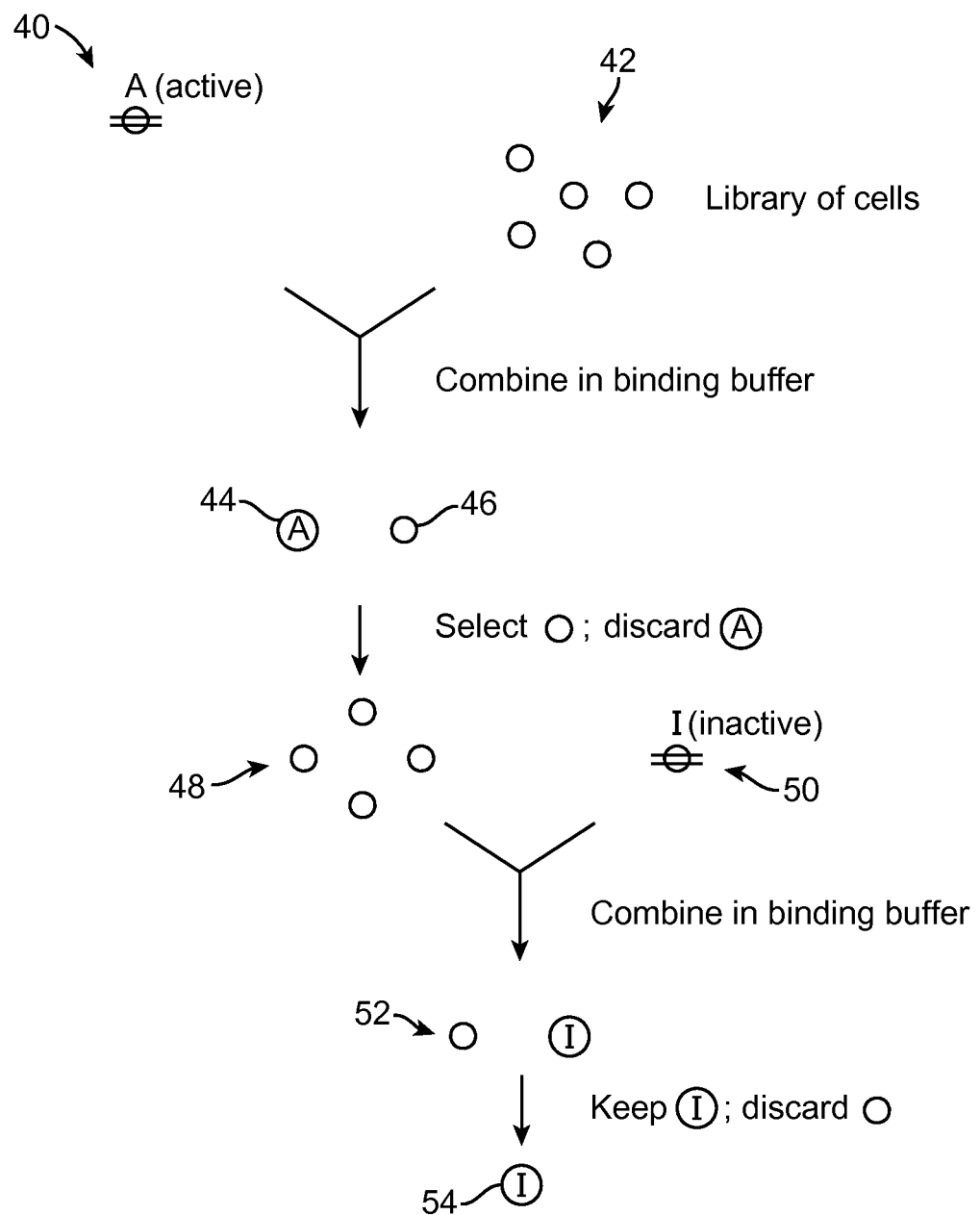
FIG. 3 schematically illustrates a further way in which one embodiment of the method can be performed.

As schematically illustrated in FIGS. 1-3, this method may be implemented in a variety of different ways.

With reference to FIG. 1, the active transmembrane receptor 2 and the inactive transmembrane receptor 4 can be distinguishably tagged; and the distinguishably tagged proteins are combined under binding conditions (i.e., in binding buffer) with a population of cells 6 that comprises a library of cell surface-tethered extracellular capture agents. Depending on the capture agent produced by each cell, some cells may bind to only the active form of the receptor 8, some cells 10 may bind to only the inactive form of the receptor, some cells 12 may bind to both the inactive and active forms of the receptor, and some cells 14 may bind to neither the inactive or active forms of the receptor. In these embodiments, cell sorting is used to select cells that are specifically bound to either the transmembrane receptor in its active conformation 16 or, alternatively, cell sorting is used to select cells that are specifically bound to the transmembrane receptor in its inactive conformation 18. Cells that bind to both the active and inactive forms of the receptor can be discarded, as can cells that bind to the other form of the receptor and cells that do not bind to any form of the receptor. In these embodiments, the cell sorting step may be done by fluorescence activated cell sorting (FACS).

In this embodiment, the distinguishable tagging may be done by conjugating the receptors to distinguishable fluorophores, or by adding different epitope tags to active and inactive receptors that allow them to be distinguished using labeled antibodies. In some embodiments, the active transmembrane receptor of and the inactive transmembrane receptor may be distinguishably tagged by (i) combining a first portion of a sample comprising the transmembrane receptor with an agonist to place said transmembrane receptor in its active conformation, and then labeling the active confirmation transmembrane receptor with a first fluorescent label: and (ii) combining a second portion of a sample with an antagonist to place said transmembrane receptor in its inactive conformation, and then labeling the inactive confirmation transmembrane receptor with a second fluorescent label that is distinguish from the first fluorescent label. Alternatively, as noted above, the inactive transmembrane receptor or the active transmembrane receptor distinguishably tagged by different epitope tags. In this embodiment, the different receptors can be distinguished from one another using labeled antibodies (as commonly used in FACS protocols).

Alternative embodiments are schematically illustrated in FIGS. 2 and 3. In these embodiments, the selection is done sequentially and, as such, need not be done with distinguishably labeled receptors (although it could be done with distinguishably labeled receptors). These embodiments may be done by MACS or FACS. As illustrated, the method illustrated in FIGS. 2 and 3 starts by binding the active form of the receptor with a population of cells that comprises a library of cell surface-tethered extracellular capture agents, and identifies cells that express capture agents that bind to the active form of the receptor (FIG. 2) or the inactive form of the receptor (FIG. 3). The method shown in FIGS. 2 and 3 may be done using the inactive form of the receptor in the first step to yield the inactive form of the receptor or the active form of the receptor, respectively.

Some embodiments of the method may involve using cell sorting to select, from an initial population of cells, a sub-population population of cells that bind to only one of the transmembrane receptors; and using cell sorting to remove, from said sub-population of cells, cells that bind to the other of said transmembrane receptors. For example, as shown in FIG. 2, the active form of the receptor 20 may be bound to an initial population of cells 22 to yield cells 24 that bind to the active form of the receptor and cells 26 that do not bind to the active form of the receptor. Cell sorting can be used to select for a sub-population of cells 28 that bind to the active form of the receptor. After the sub-population of cells 28 has been isolated, the active form of the receptor may be released from the cells, and the cells 30 are then bound to the inactive form of the receptor to produce a population of cells 32 that (because of the way that they were selected) all bind to the active form of the receptor, and that either bind to the inactive form of the receptor or do not bind to the inactive form of the receptor. Cell sorting can be used to select cells that do not bind to the inactive form of the receptor from this population (e.g., by discarding the labeled cells), thereby yielding cells 34 that only bind to the active form of the receptor.

Other embodiments of the method may involve using cells sorting to select, from an initial population of cells, a sub-population population of cells that do not bind to one of the transmembrane receptors; and using cell sorting to select, from that sub-population of cells, cells that bind to the other of said transmembrane receptors. In the exemplary method illustrated in FIG. 3, the active form of the receptor 40 may be bound to an initial population of cells 42 to yield cells 44 that bind to the active form of the receptor and cells 46 that do not bind to the active form of the receptor. Cell sorting can be used to select for a sub-population of cells 48 that do not bind to the active form of the receptor. After the sub-population of cells 48 has been isolated, the cells can be then bound to the inactive form of the receptor 50 to produce a population of cells 52 that (because of the way that they were selected) do not bind to the active form of the receptor, and that either bind to the inactive form of the receptor or do not bind to the inactive form of the receptor. Cell sorting can be used to select cells that bind to the inactive form of the receptor from this population (e.g., by discarding the unlabeled cells), thereby yielding cells 54 that only bind to the inactive form of the receptor.

After the desired cells have been isolated, the cells may be grown in culture, and the sorting step may be repeated multiples times on the cultured cells to remove false positives and false negatives. In certain cases, the cell sorting steps may be repeated several times with a successively decreasing concentration of transmembrane receptor, thereby selecting for cells that bind to the transmembrane receptor with this highest affinity. In certain cases, the capture agents expressed on the surface of the cells may be inducible and, as such, production of the capture agents may be decreased while the cells are being cultured, and then induced prior to cell selection.

As noted above, the method may be performed on any type of transmembrane receptor, such as, e.g., a GPCR, a transporter, or an ion channel. In particular embodiments, the transmembrane receptor is a GPCR. Any known GPCR can be used in the method. A disclosure of the sequences and phylogenetic relationships between 277 GPCRs is provided in Joost et al. (Genome Biol. 2002 3:RESEARCH0063, the entire contents of which is incorporated by reference), and the phylogenetic relationships between 367 human and 392 mouse GPCRs is provided in Vassilatis et al. (Proc Natl Acad Sci 2003 100:4903-8 and www.primalinc.com, each of which is hereby incorporated by reference in its entirely). GPCR families are also described in Fredriksson et al (Mol. Pharmacol. 2003 63, 1256-72).

The methods may be used to identify agents that bind to purinergic receptors, vitamin receptors, lipid receptors, peptide hormone receptors, protein receptors, non-hormone peptide receptors, non-peptide hormone receptors, polypeptide receptors, protease receptors, receptors for sensory signal mediator, and biogenic amine receptors not including β2-adrenergic receptor. In certain embodiments, said biogenic amine receptor does not include an adrenoreceptor. α-type adrenoreceptors (e.g. $\alpha_{1A}$, $\alpha_{1B}$ or $\alpha_{1C}$ adrenoreceptors), and β-type adrenoreceptors (e.g. $\beta_1$, $\beta_2$, or $\beta_3$ adrenoreceptors) are discussed in Singh et al., J. Cell Phys. 189: 257-265, 2001.

It is recognized that both native (naturally occurring) and altered native (non-naturally occurring) GPCRs may be used in the subject methods. In certain embodiments, therefore, an altered native GPCR (e.g. a native GPCR that is altered by an amino acid substitution, deletion and/or insertion) such that it binds the same ligand as a corresponding native GPCR, and/or couples to a G-protein as a result of the binding. In certain cases, a GPCR employed herein may have an amino acid sequence that is at least 80% identical to, e.g., at least 90% identical, at least 85% identical, at least 90% identical, at least 95% identical, or at least 98% identical, to at least the heptahelical domain of a naturally occurring GPCR. A GPCR employed herein may optionally contain the C-terminal domain of a GPCR. In certain embodiments, a native GPCR may be "trimmed back" from its N-terminus and/or its C-terminus to leave its heptahelical domain, prior to use.

As such, the following GPCRs (native or altered) find particular use as parental GPCRs in the subject methods: cholinergic receptor, muscarinic 3; melanin-concentrating hormone receptor 2; cholinergic receptor, muscarinic 4; niacin receptor; histamine 4 receptor; ghrelin receptor; CXCR3 chemokine receptor; motilin receptor; 5-hydroxytryptamine (serotonin) receptor 2A; 5-hydroxytryptamine (serotonin) receptor 2B; 5-hydroxytryptamine (serotonin) receptor 2C; dopamine receptor D3; dopamine receptor D4; dopamine receptor D1; histamine receptor H2; histamine receptor H3; galanin receptor 1; neuropeptide Y receptor Y1; angiotensin II receptor 1; neurotensin receptor 1; melanocortin 4 receptor; glucagon-like peptide 1 receptor; adenosine A1 receptor; cannabinoid receptor 1; and melanin-concentrating hormone receptor 1.

In particular embodiments, the GPCR may belong to one of the following GPCR families: amine, peptide, glycoprotein hormone, opsin, olfactory, prostanoid, nucleotide-like, cannabinoid, platelet activating factor, gonadotropin-releasing hormone, thyrotropin-releasing hormone or melatonin families, as defined by Lapinsh et al (Classification of G-protein coupled receptors by alignment-independent extraction of principle chemical properties of primary amino acid sequences. Prot. Sci. 2002 11:795-805). The subject GPCR may be a family A GPCR (rhodopsin-like), a family B GPCR (secretin-like, which includes the PTH and glucagon receptors), a family C GPCR (glutamate receptor-like, which includes the GABA glutamate receptors), or an "other" family GPCR (which includes adhesion, frizzled, taste type-2, and unclassified family members).

Exemplary GPCRs that can be used in the subject include, but are not limited to 5-HT1A, 5-HT1B, 5-HT1D, 5-ht1e, 5-HT1F, 5-HT2A, 5-HT2B, 5-HT2C, 5-HT4, 5-ht5a, 5-HT6, 5-HT7, M1, M2, M3, M4, M5, A1, A2A, A2B, A3, alpha 1A-adrenoceptor, alpha 1B-adrenoceptor, alpha 1D-adrenoceptor, alpha 2A-adrenoceptor, alpha 2B-adrenoceptor, alpha 2C-adrenoceptor, beta 1-adrenoceptor, beta 2-adrenoceptor, beta 3-adrenoceptor, C(3a, C5a, C5L2, AT1, AT2, APJ, GPBA, BB1, BB2, BB3, B1, B2, CB1, CB, B2 CCR1, CCR2, CCR3, CCR4, CCR5S, CCR6, CCR7, CCR8, CCR9, CCR10, CXCR1, CXCR2, CXCR3, CXCR4, CXCR5, CXCR6, CXCR7, CX3CR1, XCR1, CCK1, CCK2, D1, D2, D3, D.sub.4, D5, ETA, ETB, GPER, FPR1, FPR2/ALX, FPR3, FFA1, FFA2, FFA3, GPR42, GAL1, GAL2, GAL3, ghrelin, FSH, LH, TSH, GnRH, CGnRH2, H1, H2, H3, H4, HCA1, HCA2, HCA3, kisspeptin, BLT1, BLT2, CysLT1, CysLT2, OXE, FPR2/ALX, LPA1, LPA2, LPA3, LPA4, LPA5, S1P1, S1P2, S1P3, S1P4, SIPS, MCH1, MCH2, MC1, MC2, MC3, MC4, MC5, MT1, MT2, motilin, NMU1, NMU2, NPFF1, NPFF2, NPS, NPBW1, NPBW2, Y1, Y2, Y4, Y5, NTS1, NTS2, delta, kappa, mu, NOP, OX1, OX2, P2Y1, P2Y2, P2Y4, P2Y6, P2Y11, P2Y12, P2Y13, P2Y14, QRFP, PAF, PKR1, PKR2, PRRP, DP1, DP2, EP1, EP2, EP3, EP4, FP, IP1, TP, PAR1, PAR2, PAR3, PAR4, RXFP1, RXFP2, RXFP3, RXFP4, sst1, sst2, sst3, sst4, sst5, NK1, NK2, NK3, TRH1, TA1, UT, V1A, V1B, V2, OT, CCRL2, CMKLR1, GPR1, GPR3, GPR4, GPR6, GPR12, GPR15, GPR17, GPR18, GPR19, GPR20, GPR21, GPR22, GPR25, GPR26, GPR27, GPR31, GPR32, GPR33, GPR34, GPR35, GPR37, GPR37L1, GPR39, GPR42, GPR45, GPR50, GPR52, GPR55, GPR61, GPR62, GPR63, GPR65, GPR68, GPR75, GPR78, GPR79, GPR82, GPR83, GPR84, GPR85, GPR87, GPR88, GPR101, GPR119, GPR120, GPR132, GPR135, GPR139, GPR141, GPR142, GPR146, GPR148, GPR149, GPR1500, GPR11, GPR51, GPR152, GPR153, GPR160, GPR161, GPR162, GPR171, GPR173, GPR174, GPR176, GPR182, GPR183, LGR4, LGR5, LGR6, LPAR6, MAS1, MAS1L, MRGPRD, MRGPRE, MRGPRF, MRGPRG, MRGPRX1, MRGPRX2, MRGPRX3, MRGPRX4, OPN3, OPN5, OXGR1, P2RY8, P2RY10, SUCNR1, TAAR2, TAAR3, TAAR4, TAAR5, TAAR6, TAAR8, TAAR9, CCPB2, CCRL1, FY, CT, calcitonin receptor-like, CRF1, CRF2, GHRH, GIP, GLP-1, GLP-2, glucagon, secretin, PTH1, PTH2, PAC1, VPAC1, VPAC2, BAI1, BAI2, BAI3, CD97, CELSR1, CELSR2, CELSR3, ELTD1, EMR1, EMR2, EMR3, EMR4P, GPR56, GPR64, GPR97, GPR98, GPR110, GPR111, GPR112, GPR113, GPR114, GPR115, GPR116, GPR123, GPR124, GPR125, GPR126, GPR128, GPR133, GPR143, GPR144, GPR157, LPHN1, LPHN2, LPHN3, CaS, GPRC6, GABAB1, GABAB2, mGlu1, mGlu2, mGlu3, mGlu4, mGlu5, mGlu6, mGlu7, mGlu8, GPR156, GPR158, GPR179, GPRC5A, GPRC5B, GPRC5C, GPRC5D, frizzled, FZD1, FZD2, FZD3, FZD4, FZD5, FZD6, FZD7, FZD8, FZD9, FZD10, SMO. In certain embodiments, the method may use the β2-adrenergic receptor (β 2AR), the A2A-Adenosine Receptor ($A_2A$), S1P1, an opioid receptor (OLR), e.g., NOP1, a chemokine receptor, e.g., CXCR3 or CCR5 (CCR5), GLP1R, PTHR1, LPA1, LPA2, LPA3, S1P2, S1P3, S1P4, or SIPS. The GPCR used may be of any class, e.g., Class A (rhodopsin-like); Class B (secretin-like); Class C (metabotropic glutamate/pheromone); cAMP receptors vomeronasal receptors (V1R and V3R); and taste receptors T2R. GPCRs to be evaluated include, but are not limited to, a class A GPCR, a class B GPCR, a class C GPCR, a class D GPCR, a class E GPCR, and a class F GPCR.

The population of cells comprising a library of cell surface-tethered extracellular capture agents used in the method can be produced by any suitable method that provides a library of cells in which the candidate capture agents are displayed on the surface of a cell. Surface display methods are reviewed in Witrrup et al (Curr. Opin. Biotechnol, 2001 12:395-399) and include display on bacteria (Georgiou et al., Nat. Biotechnol. 1997 15:29-34; Georgiou et al., Trends Biotechnol. 1993 11:6-10; Lee et al., Nat. Biotechnol. 2000 18:645-648; June et al., Nat. Biotechnol. 1998 16:576-80), yeast (Boder and Wittrup, Methods Enzymol. 2000 328:430-44; Boder and Wittrup, Nat. Biotechnol. 1997 15:553-557), and mammalian cells (Whitehorn et al., Bio/technology 1995 13:1215-1219). In certain embodiments, the population of cells are yeast cells. Methods for displaying protein libraries on yeast cells may be performed in accordance with any of the techniques known to those skilled in the art. See U.S. Pat. Nos. 6,423,538; 6,114,147; and 6,300,065; as well as Boder et al (Nat. Biotechnol. 1997 15:553-7), Boder et al (Biotechnol. 1998 14:55-62), Boder et al (Methods Enzymol. 2000 328:430-44), Boder et al (Proc. Natl. Acad. Sci. 2000, 97:10701-5), Shusta et al (Nat. Biotechnol., 1998, 16:773-7), Shusta et al (J. Mol. Biol. 1999 292:949-56); Shusta et al (Curr. Opin. Biotechnol., 1999 10:117-22), Shusta et al (Nat. Biotechnol. 2000 18:754-9); Wittrup et al (Ann. N.Y. Acad. Sci. 1994 745: 321-30), Wittrup et al. (Cytometry, 1994 16:206-13); Wittrup (Curr. Opin. Biotechnol. 1995 6:203-8); Wittrup (Trends Biotechnol. 1999 17:423-4); Wittrup (Nat. Biotechnol. 2000 18:1039-40); Wittrup (Curr. Opin. Biotechnol. 2001 12:395-9), all of which are incorporated herein by reference in their entirety.

In certain embodiments, the population of cells may display a library of single chain antibodies. In particular cases, the single chain antibodies may be made by immunizing a suitable animal (e.g., a camelid (e.g., a camel, llama or alpaca) or a cartilaginous fish (e.g., a shark)) with an active or inactive form of the transmembrane receptor (as described in Rasmussen (Nature 2011 469: 175-180)), where the choice of whether to use an active or inactive form of the receptor is dictated by whether on wishes to obtain antibodies that bind to the active or inactive form of the transmembrane receptor. In an exemplary embodiment, an animal, e.g., a llama, can immunized with a purified agonist or antagonist bound receptor reconstituted at high density into phospholipid vesicles. After a suitable immune response has been mounted, cDNAs encoding the antibody repertoire from the immunized animal may be cloned en masse into an expression vector suitable for expressing the antibodies on the surface of the host cell, thereby making a population of cells that can be used in the method.

In some embodiments, the library of cell surface-tethered extracellular capture agents can be a library of variants of a binding agent that is known to bind said transmembrane receptor in its active or inactive conformation and not bind the transmembrane receptor in the other conformation. This embodiment may be used to obtain a capture agent that has a higher affinity using the sequence of an initial capture agent that has a lower affinity. This library can be made from an initial capture agent by any suitable mutagenesis methods such that those described in, e.g., Otten et al (Biomolecular Engineering 2005 22: 1-9), Reetz et al (Nature Prot. 2007 2: 891-903), Stemmer (Nature 1994 370: 389-391) and Labrou et al (Curr. Protein Pept. Sci. 2010 11: 91-100). In certain embodiments, the method may involve error-prone PCR or DNA shuffling, for example and in particular cases may be adapted from phage display, enzyme engineering or zinc finger technologies. Many molecular techniques may be employed in this method, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic," fragmentation, see, e.g., U.S. Pat. Nos. 6,291,242; 6,287,862; 6,287,861; 5,955,358; 5,830, 721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly (e.g., GeneReassembly, see, e.g., U.S. Pat. No. 6,537,776), gene site saturation mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

Once a cell that displays a capture agent that selectively binds to either the active or inactive form of the receptor has been isolated, it may be cultured, and the method may further involve isolating nucleic acid encoding at least the binding region of the cell surface-tethered extracellular capture agent from a cell. The nucleic acid may be sequenced, thereby providing the amino acid sequence of the binding region of the capture agent. The method may further involve expressing the binding region of the cell surface-tethered extracellular capture agent in a second host cell and, in certain cases, measuring the affinity of the binding region to a transmembrane receptor its active or inactive conformation relative to the same transmembrane receptor in the other conformation.

Exemplary pairs of agonists and antagonists that can be used in the method are set forth below, and/or in the references cited below. For other receptors, suitable pairs of agonists and antagonists may be known in the art. The references cited below are incorporated by reference for all purposes, in particular for disclosure of agonists and antagonists, and conditions by which those compounds bind to their receptors.

| Receptor | Agonist | Antagonist |
|---|---|---|
| $M_2$ muscarinic receptor | Acetylcholine[1] | Atropine[1] |
| $\beta_2$ adrenergic receptor | Fenoterol[2] | Propranolol[3] |
| CXCR4 chemokine receptor | SDF-1$\alpha$[4] | SDF-1$\alpha$ mutant[4] |
| C5a receptor | C5a[5] | L156,602[5] |
| $\mu$ opioid receptor | Morphine[6] | Naloxone[7] |
| Protease-activated receptor 1 | Thrombin treatment[8] | Vorapaxar[8] |
| H1 histamine receptor | Histamine[9] | Diphenhydramine[10] |
| $A_{2a}$ adenosine receptor | Adenosine[11] | Caffeine[12] |
| $D_2$ dopamine receptor | Dopamine[13] | Raclopride[14] |
| Angiotensin II type 1 receptor | Angiotensin I[15] | Irbesartan[16] |
| Apelin receptor | Apelin[17] | ALX40-4C[18] |
| Cannabinoid receptor 1 | Cannabindiol[19] | Rimonabant[20] |
| Endothelin A receptor | Endothelin 2[21] | A-127722[22] |
| Thyroid-stimulating hormone receptor | Thyroid-stimulating hormone[23] | Monoclonal antibodies[23] |
| Melanocortin receptor 1 | MS05[24] | Agouti protein[25] |
| Somatostatin receptor 1 | SOM230[26] | BIM-23627[27] |
| Glucagon receptor | Glucagon[28] | des-His(1)-[Glu9]glucagon-NH2 [29] |
| $V_2$ vasopressin receptor | AVP[30] | Tolvaptan[31] |
| Melatonin receptor 1 | Melatonin[32] | Luzindol[33] |
| Ghrelin receptor | Ghrelin[34] | BIM28163[35] |
| Parathyroid hormone receptor 1 | PTH[36] | TIP39[37] |
| Prostaglandin D2 receptor | PGD2[38] | Ramatroban[39] |

[1]Kovacs et al, 1998 *J Pharmacol Exp Ther*, 284: 500-507.
[2]January et al 1997 *J Biol Chem*, 272: 23871-23879.
[3]Louis et al *Eur J Pharmacol*, 367: 431-435.
[4]Loetscher et al 1998 *J Biol Chem*, 273: 22279-22283.
[5]Monk et al 2007 *British Journal of Pharmacology* 152 (4): 429-48.
[6]Toll et al 1998, *NIDA Res Monogr.* 178: 440-66
[7]Raynor at al 1994 *Mol Pharmacol*, 45: 330-334.
[8]Chackalamannil et al 2008 *Journal of Medicinal Chemistry* 51 (11): 3061-4.
[9]Moguilevsky et al 1994 *Eur J Biochem*, 224: 489-495.
[10]Booth et al 2002 *J Pharmacol Exp Ther*, 302: 328-336.
[11]Yan et al 2003 *Expert Opin Emerg Drugs*, 8 (2): 537-76.
[12]Kull et al 1999 *Biochem. Pharmacol.*, 57: 65-75.
[13]Freedman 1994 *J Pharmacol Exp Ther*, 268: 417-426.
[14]Schetz 2000 *Mol Pharmacol*, 57: 144-152. [
[15]de Gasparo et al 1994 Heterogeneity of angiotensin receptor subtypes. in Medicinal Chemistry of the Renin-Angiotensin System. Edited by Timmermanns, P. B. M. W. M. and Wexler, R. R. Elsevier. 269-294.
[16]Vanderheyden et al 1999 *Br. J. Pharmacol.*, 126: 1057-1065.
[17]Hosoya et al 2000 *J Biol Chem.*, 275: 21061-21067.
[18]Zhou et al 2003 *Virology.*, 307: 22-36.
[19]Felder et al 1995*Mol. Pharmacol.*, 48: 443-450.
[20]Felder et al 1998 *J. Pharmacol. Exp. Ther.*, 284: 291-297.
[21]Maguire et al 1995 *Br. J. Pharmacol.*, 115: 191-197.
[22]Opgenorth et al 1996 *J. Pharmacol. Exp. Ther.*, 276: 473-481.
[23]Costagliola et al 2004 *Mol Endocrinol*, 18: 3020-3034.
[24]Szardenings et al 2000 *Peptides.*, 21: 239-243.
[25]Lu et al 1994 *Nature*, 371: 799-802.
[26]Schmid et al *Neuroendocrinology*, 80: 47-50.
[27]Tulipano et al 2002 *Endocrinology*, 143: 1218-1224.
[28]Pohl et al 1969. *Science*, 164: 566-567.
[29] Unson et al 1987 *Proc. Natl. Acad. Sci. U.S.A.*, 84: 4083-4087.
[30]Cotte et al 1998 *J Biol Chem*, 273: 29462-29468.
[31]Yamamura et al 1998 *J Pharmacol Exp Ther*, 287: 860-867.

| Receptor | Agonist | Antagonist |
| --- | --- | --- |

[32]Audinot et al 2003 *Naunyn Schmiedebergs Arch Pharmacol*, 367: 553-561.
[33]Audinot et al 2003 *Naunyn Schmiedebergs Arch Pharmacol*, 367: 553-561.
[34]Muccioli et al 2001 *J Endocrinol Invest.*, 24: RC7-RC9.
[35]Halem et al 2004 *Eur J Endocrinol.*, 151: S71-S75.
[36]Gardella et al 1995 *J Biol Chem*, 270: 6584-6588.
[37]Jonsson et al 2001*Endocrinology*, 142: 704-709.
[38]Hata et al 2003 *J Pharmacol Exp Ther*, 306: 463-470.
[39]Sugimoto et al 2005 *Eur J Pharmacol*, 524: 30-37.

Figure 4:
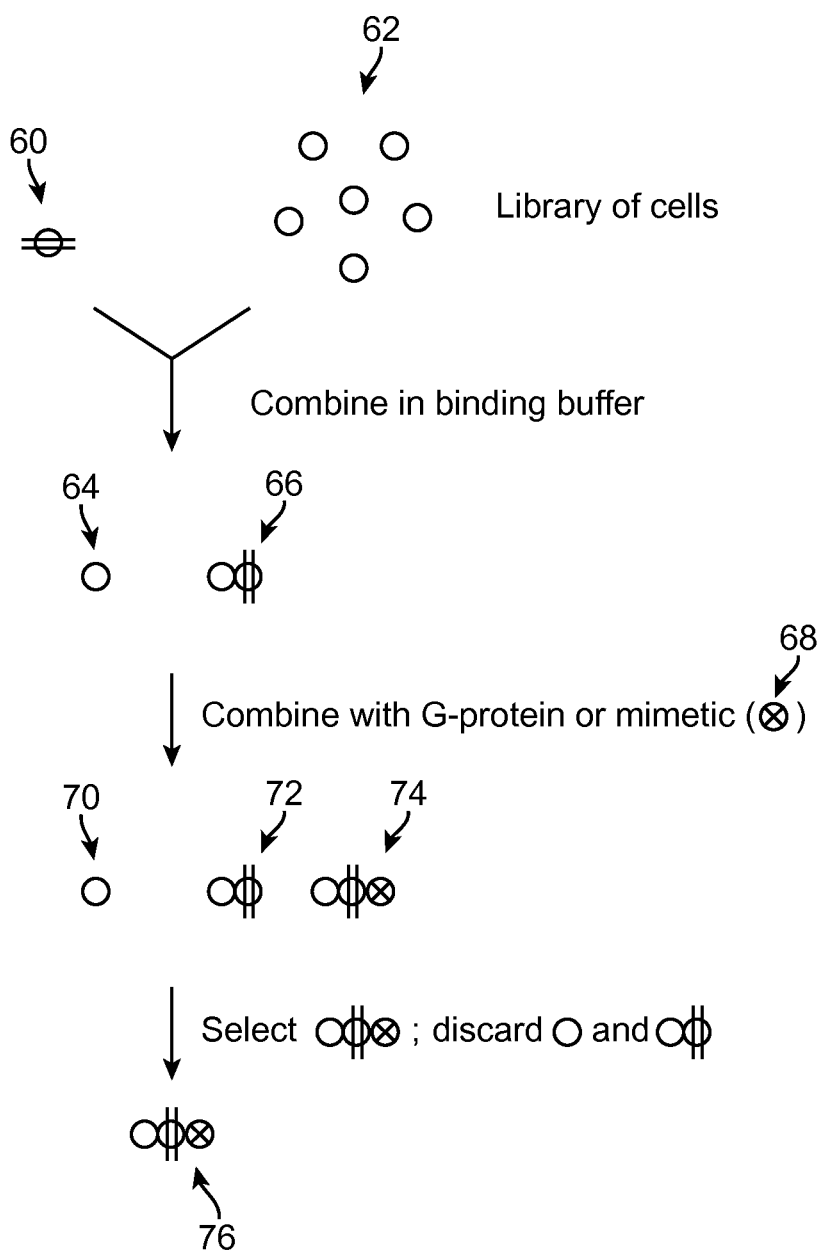
FIG. 4 schematically illustrates one way in which another embodiment of the method can be performed.

Also provide herein is a method by which agonists or antagonists of a GPCR can be identified. As illustrated in FIG. 4, this method comprises: contacting a GPCR 60 (which may be not bound to any ligand) with a population of cells that comprise a library of surface-tethered extracellular proteins 62. This step should be done under conditions by which the GPCR binds to the surface-tethered extracellular proteins on the cells, and should result in a first population 64 that does not bind to the receptor, and a second population 66 that does bind to the receptor. These cells can be labeled with a G-protein (which only binds to the active conformation of the GPCR) or mimetic thereof 68 that specifically binds to the GPCR in its active or inactive state, but not both. This labeling should result in three populations of cells: a first population 70 that is neither bound to the GPCR or the G-protein or mimetic thereof, a second population 72 that is bound to the GPCR not the G-protein or mimetic thereof, and third population 74 that is bound to the GPCR and the G-protein or mimetic thereof. Cells that bound to the GPCR and the G-protein or mimetic thereof can be isolated by cell sorting produce a cell population of cells 76 that produce extracellular proteins that place a GPCR in one conformation (i.e., the active or inactive conformation) but not the other. Depending on how the method is performed, the method may be used to identify agonists or antagonists of a GPCR. The nucleic acid encoding an identified protein can be cloned, sequenced and expressed in a heterologous system and/or mutagenized in a similar way to the capture agents described above.

Depending on how the method is done, the G-protein or mimetic thereof can be bound to the G-protein at any time in the method, e.g., before the G-protein is contacted with the cells, or afterwards, prior to cell sorting. If the G-protein or mimetic thereof is fluorescently labeled, the labeling should be done before the G-protein or mimetic thereof is contacted with the cells. If an antibody is used, the G-protein or mimetic thereof can be labeled after the G-protein or mimetic thereof is contacted with the cells. The G-protein or mimetic thereof used in the method can be labeled with a fluorophore or using a labeled antibody, in a similar way to as described above. The labeled G-protein may a heterotrimer G-protein comprising $G_s$, $G_i$, $G_q$, $G_{12}$ or $G_t$, stabilized in the presence of GDP. In certain cases, the proteins that make up the heterotrimeric G-protein may be combined with one another in the presence of GDP, and then, after complex has been stabilized, the uncomplexed GDP can be removed using apyrase.

The G-protein or mimetic thereof used in the method can be, e.g., the G-protein to which the GPCR used in the method usually binds (see the list above). If a mimetic is used, then the mimetic may be a conformation-specific capture agent such as that described above, e.g., a single chain antibody that either binds to the active or inactive conformation of the GPCR. In one exemplary embodiment, the cells may be bound to an unlabeled GPCR and then stained with labeled antibody (e.g., a single chain antibody) directed to G protein in its active state. In another exemplary embodiment, the cells may be bound to an unlabeled GPCR and then stained with labeled antibody (e.g., a single chain antibody) directed to G protein in its inactive state.

Again, this method may be done using any suitable cell type, including yeast cells, using FACS or MACS, descriptions of which are set forth above. The cell population used in the method may be any a library of surface-tethered extracellular proteins which, in certain cases, may be a library of surface-tethered capture agents as discussed above. Methods for making protein libraries are known in the art. In certain cases, the proteins of the library may be at least 10 amino acids in length, e.g., 10 to 100 or 10 to 1,000 amino acids in length.

The agents identified by the methods described above have a number of valuable applications. For example, capture agents identified by the method can be used crystallize a receptor in its inactive or active state in a similar manner to that described in Steyaert and Kobilka (Curr. Opin. Struct. Biol. 2011 21:567-72), Deupi and Standfuss (Curr. Opin. Struct. Biol. 2011 21:541-51) and Rasmussen et al Nature 2011 469: 175-80. The capture agents can potentially be used to modulate the activity of a receptor, or, as described above, the capture agents can be used in a method that identifies modulators of the receptor.

Compositions

In addition to the methods described above, also provided herein is a composition that comprises a cell, a complex comprising a GPCR and modulator of said GPCR, wherein the GPCR is maintained in an active or inactive conformation by the modulator; detergent, and cholesterol or an analog thereof. The detergent, which may be present at a concentration of 0.005% to 0.15% (w/v), e.g., 0.5 to 0.13 (w/v), 0.8 to 0.12% (w/v) or 0.8 to 0.12% (w/v), may be a maltoside detergent (e.g., an alkyl maltoside such as decyl-maltoside or dodecyl maltoside), a neopentoglycol detergent (e.g., decyl maltose neopentyl glycol, lauryl maltose neopentyl glycol or octyl glucose neopentyl glycol) or a glyco-lithocholate (GLC) or glyco-diosgenin (GDN) amphiphile (e.g., GDN, GLC-1, GLC2 or GLC-3, as described in Chae et al Chem. Eur. J. 2012 18: 9485-9490). Alternatively, the GPCR could be solubililzed in HDL particles or nanodiscs. The cholesterol or analog thereof (e.g., cholesterol succinate or cholesterol hemisuccinate) may be at a concentration of 0.005% to 0.02%, e.g., 0.008% to 0.013% or 0.09% to 0.011%. The cholesterol or analog thereof may be included because it helps to stabilize the receptor and prevent denaturation. Many (although not all) GPCRs contain cholesterol binding sites, and this compound binds those sites and stabilizes the receptor. In some cases, the cholesterol or analog thereof is not required.

In certain cases, the components described above may be in a binding buffer that comprises salt (e.g., NaCl or KCl at a concentration of 50 mM to 500 mM NaCl, e.g., 100 mM to 200 mM) and that is buffered, e.g., by phosphate, Tris, or HEPES, at a pH of pH 7-8. The buffer may also contain BSA (0.5% to 2% w/v) or another protein additive to stabilize the protein selection reagents, and EDTA (0.5 to 2 mM which prevents aggregation of the cells). The binding buffer may also contain a concentration of detergent and/or lipid to match the concentrations of these reagents that best stabilize the receptor as described above (e.g., 0.1% w/v DDM or 0.02% w/v MNG).

As noted above, the cells may be bacterial, yeast or mammalian cells for example. In certain cases, the cells may be at a concentration of $1\times10^7$-$2.5\times10^9$ cells/ml.

In particular cases, the composition may comprise a population of cells comprising a library of cell surface-tethered extracellular capture agents, as described above. The population may contain at least $10^6$, at least $10^7$ or at least $10^8$ different cells, where at least one of the cells is bound to the GPCR via the binding region of the capture agent displayed on the surface of that cell. Such a cell can be selected by FACS or MACS, as discussed above.

Although the foregoing embodiments have been described in some detail by way of illustration and example for purposes of clarity of understanding, it is readily apparent to those of ordinary skill in the art in light of the above teachings that certain changes and modifications can be made thereto without departing from the spirit or scope of the appended claims.

EXAMPLES

Aspects of the present teachings can be further understood in light of the following example, which should not be construed as limiting the scope of the present teachings in any way.

Methods I

β$_2$-Adrenergic Receptor Expression and Purification:

Human β$_2$-adrenergic receptor bearing an amino-terminal FLAG epitope tag and truncated after residue 365 was expressed in Sf9 cells using the BestBac baculovirus system (Expression Systems; Davis, Calif.). Cells were infected at a density of $4\times10^6$ cells/mL, then incubated for two days at 27° C. Receptor was extracted as described previously (See, e.g., Kobilka et al, Analytical Biochemistry 1995 231, 269-271). Receptor was first purified by FLAG affinity chromatography, then labeled with a 10-fold molar excess of biotin-PEG$_{11}$-maleimide (Thermo Scientific; Rockford, Ill.), which reacts with the endogenous residue Cys265. Following a one hour incubation at room temperature, unlabeled receptor was blocked with 2 mM iodoacetamide for 15 minutes. Receptor was then purified by alprenolol sepharose chromatography to isolate only functional receptor. Alprenolol sepharose eluate was concentrated on FLAG affinity resin, then washed with ligand-free buffer for 30 minutes at room temperature to eliminate bound alprenolol. Detergent was gradually exchanged from dodecyl maltoside (DDM) to lauryl maltose neopentyl glycol (MNG) by washing in buffer containing decreasing amounts of DDM and MNG at a fixed concentration of 0.1% (w/w). Receptor was eluted, aliquoted, and frozen in 20% glycerol.

Display and Functional Evaluation of Nanobody 80 on Yeast:

Nanobody 80 (Nb 80) was cloned into the C-terminal Aga2 yeast-display vector pYAL (Wang et al, PEDS 2005 18(7):337-343) and transformed and displayed on yeast as previously described (see, e.g., Chao, G. et al. Nature protocols 2006 1, 755-768). Induced yeast displaying Nb 80 were washed with PBE buffer (phosphate buffered saline with 0.5 mM EDTA and 0.5% BSA) supplemented with 0.02% MNG detergent (PBEM buffer) and stained with varying concentrations of biotinylated β2 receptor liganded with either the high-affinity agonist BI-167107 or the high-affinity antagonist carazolol for one hour at 4° C. The yeast were then washed with PBEM buffer and stained with Alexa647-conjugated streptavidin for 15 minutes at 4° C. Mean cell fluorescence was measured using the FL-4 channel of an Accuri C6 flow cytometer.

Construction of Nb80 Affinity-Maturation Library:

The affinity-maturation library was assembled by assembly PCR with oligonucleotide primers (Table 1) containing degenerate codons at 15 distinct positions (Table 2). The PCR product was further amplified with primers containing homology to pYal. Mutagenic nanobody DNA and linearized pYAL vector were co-electroporated into EBY100 yeast to yield a library of $0.8\times10^8$ transformants.

TABLE 1

Nb80 affinity maturation library assembly and amplification primers

| Primer | Sequence |
| --- | --- |
| N80SR1F | ATGGCCCAGGTGCAGCTGCAGGAGTCTGGGGGA GGCTTGGTGCA (SEQ ID NO: 1) |
| N80SR2R | AGAGGCTGCACAGGAGAGTCTCAGAGACCCCCC AGCCTGCACCAAGCCTCCCC (SEQ ID NO: 2) |
| N80SR3F | CTCTCCTGTGCAGCCTCTGGARSCATCYWCRST NTCAATRYCATGGGCTGGTACCGCCAGG (SEQ ID NO: 3) |
| N80SR4R | CGACCAACTCGCGCTGCTTCCCTGGAGCCTGGC GGTACCAGCCCATG (SEQ ID NO: 4) |
| N80SR5F | GCAGCGCGAGTTGGTCGCARYTATTYWTAGTGG TGGTWMCACANACTATGCCAACTCCGTGAAG (SEQ ID NO: 5) |
| N80SR6R | GCATTGTCTCTGGAGATGGTGAATCGGCCCTTC ACGGAGTTGGCATAGT (SEQ ID NO: 6) |
| N80SR7F | CACCATCTCCAGAGACAATGCCGCGAACACGGT GTATCTGCAAATGAACAGCCTGAAAC (SEQ ID NO: 7) |
| N80SR8R | CCTTTACATTACAGTAATAGACGGCCGTGTCCT CAGGTTTCAGGCTGTTCATTTGCAGATA (SEQ ID NO: 8) |
| N80SR9F | GCCGTCTATTACTGTAATGTAAAGGACYWCGGG RSTNTCNTTYWTRAWTATGACTACTGGGGCCAG (SEQ ID NO: 9) |
| N80SR10R | TGAGGAGACGGTGACCTGGGTCCCCTGGCCCCA GTAGTCATA (SEQ ID NO: 10) |
| pYa1NB80AMPF | CATTTTCAATTAAGATGCAGTTACTTCGCTGTT TTTCAATATTTTCTGTTATTGCTAGCGTTTTAG CAATGCCCAGGTGCAGCTGCAGGAG (SEQ ID NO: 11) |
| pYa1NB80AMPR | CCACCAGATCCACCACCACCCAAGTCTTCTTCG GAGATAAGCTTTTGTTCGGATCCTGAGGAGACG GTGACCTGGGTCCC (SEQ ID NO: 12) |

TABLE 2

Library design of Nb80 affinity maturation library

| Mutation # | Residue | Degenerate Codon | Possible A.A. |
|---|---|---|---|
| 1 | S29 | RSC | S/T/A/G |
| 2 | F31 | YWC | F/Y/H/L |
| 3 | S32 | RST | S/T/A/G |
| 4 | I33 | NTC | F/I/L/V |
| 5 | T35 | RYC | T/I/V/A |
| 6 | A52 | RYT | T/I/V/A |
| 7 | H54 | YWT | F/Y/H/L |
| 8 | S58 | WMC | S/N/T/Y |
| 9 | N60 | NAC | N/D/H/Y |
| 10 | Y102 | YWC | F/Y/H/L |
| 11 | A104 | RST | S/T/A/G |
| 12 | V105 | NTC | F/I/L/V |
| 13 | L106 | NTT | F/I/L/V |
| 14 | Y107 | YWT | F/Y/H/L |
| 15 | E108 | RAW | E/D/K/N |

Library Selection with Detergent-Solubilized $\beta_2$ Receptor:

For the first round of selection, $1.0 \times 10^9$ yeast induced with SGCAA medium were washed with PBEM buffer and then resuspended in 5 mL of PBEM buffer containing 200 nM biotinylated $\beta_2$ receptor liganded with BI-167107. After one hour of incubation at 4° C. with rotation, yeast were washed with PBEM buffer, and then stained with Alexa647-conjugated streptavidin in PBEM buffer for 15 minutes at 4° C. Yeast were washed again with PBEM buffer and magnetically labeled with 250 μL anti-647 microbeads (Miltenyi) in 4.75 mL PBEM buffer for 15 minutes at 4° C. Yeast were washed a final time and labeled yeast were isolated by magnetic selection with an LS column (Miltenyi) pre-equilibrated with PBEM buffer. Magnetically-sorted yeast were resuspended in SDCAA medium and cultured at 30° C.

Rounds 2-6 were selected in a similar manner, with the following modifications. Prior to positive selection with agonist-occupied $\beta_2$ receptor, negative selection with antagonist-bound receptor was performed to select for clones that maintained a preference for the 'active' state of the $\beta_2$ receptor. Briefly, $1.0 \times 10^8$ yeast were washed with PBEM buffer and resuspended in 500 μL PBEM buffer containing 1 μM biotinylated $\beta_2$ receptor liganded with carazolol. Yeast were incubated at 4° C. for one hour, then labeled with Alexa647 or PE-conjuaged streptavidin, and magnetically labeled with 50 μL of the respective anti-fluorophore microbeads (Miltenyi) in 450 μL PBEM buffer. Magnetically-labeled yeast were applied to an LS column and the depleted flow-through was collected for subsequent positive selection. In this manner, yeast clones binding the 'inactive,' antagonist-occupied receptor were discarded. Positive selections on for 'active,' agonist-occupied receptor were performed as for round one, but in a staining volume of 500 μL and with successively decreasing concentrations of BI-167107-bound β2 receptor: 200 nM receptor for rounds 2 and 3, 20 nM receptor for round 4, and 1 nM receptor for round 5. For round 6, positive selection was performed by a kinetic selection strategy to select for clones with the slowest off-rates. Briefly, yeast were stained with 200 nM biotinylated BI-167107-bound β2 receptor for one hour, washed with PBEM, and then resuspended in 500 μL PBEM containing 1 μM non-biotinylated BI-167107-bound $\beta_2$ receptor. The cells were incubated at 25° C. for 155 minutes, after which they were washed with ice-cold PBEM and stained with fluorescently-labelled streptavidin. Enrichment with magnetic separation for rounds 2-6 was performed as for round 1, but with 50 μL anti-fluorophore magnetic microbeads with 450 μL PBEM buffer. Subsequent to round 6, post-sorted yeast were plated onto SDCAA-agar plates, colonies were picked and cultured in liquid SDCAA medium, and the plasmids encoding the nanobodies were isolated with a ZymoPrep Yeast Plasmid Miniprep II kit (Zymo Research) and sequenced.

Expression of Nanobodies in *E. coli*

Nanobodies were cloned into the periplasmic expression vector pET26B, containing an amino terminal signal sequence a carboxy terminal 8× Histidine tag and transformed into BL-21(DE3) *E. coli*. Cells were induced in Terrific Broth at an $OD_{600}$ of 0.8 with 1 mM IPTG and incubated with shaking at 22° C. for 24 hours. Periplasmic protein was obtained by osmotic shock and the nanobodies were purified using nickel-nitrilotriacetic acid (Ni-NTA) chromatography. Eluted nanobodies were digested with carboxypeptidase A to remove His tag.

Surface Plasmon Resonance (SPR):

Experiments were conducted with a Biacore T100 at 25° C. Protein concentrations were quantified by 280 nm absorbance with a Nanodrop2000 spectrometer (Thermo Scientific). Biotinylated BI-167107-bound $\beta_2$ receptor was immobilized on an SA sensorchip (GE) at an Rmax of approximately 40 relative units (RU). Biotinylated $M_2$ muscarinic receptor bound to tiotropium was immobilized with an RU value matching that of the reference surface to control for nonspecific binding. Measurements were made using with serial dilutions of Nb80 or Nb6B9 in HBSM (10 mM HEPES pH 7.4, 150 mM NaCl, 0.01% MNG) using single-cycle kinetics. All data were analyzed with the Biacore T100 evaluation software version 2.0 with a 1:1 Langmuir binding model.

Bimane Fluorescence Assay:

$\beta_2$ receptor truncated at residue 365 was expressed in Sf9 cells and purified by FLAG affinity chromatography as described above. It was then labeled with 10 μM monobromobimane (mBBr) for 1 hr at room temperature. The reaction was terminated by the addition of 2 mM cysteine, then receptor was purified by alprenolol sepharose as described above. Receptor was diluted to 100 nM in a buffer containing 0.1% DDM, 0.01% CHS, 100 mM NaCl, 20 mM HEPES pH 7.5 in a 0.5 mL fluorescence cuvette. Fluorescence assays were performed as described previously (See, e.g., Yao et al. Proceedings of the National Academy of Sciences 106, 9501-9506 (2009).

Radioligand Binding Assays:

$\beta_2$ receptor truncated at residue 365 was expressed and purified as described above. Prior to final elution from FLAG resin the receptor was washed for 30 minutes in buffer containing no alprenolol. Receptor was then reconstituted into HDL particles comprised of apolipoprotein A1 and a 3:2 (mol:mol) mixture of POPC:POPG lipid. Binding reactions were 500 μL in volume, and contained 50 fmol functional receptor, 0.5 nM $^3$H dihydroalprenolol, 100 mM NaCl, 20 mM HEPES pH 7.5, 0.1% BSA, and ligands and nanobodies as indicated. Reactions were mixed, then incubated for four hours prior to filtration with a Brandel 48-well harvester onto a filter pre-treated with 0.1% polyethylenimine. Radioactivity was measured by liquid scintillation counting. All measurements were performed in triplicate.

G Protein Complex Formation In Vitro:

Heterotrimeric G protein was expressed in insect cells with native lipid modifications, purified in detergent-containing buffer, then concentrated to a concentration of 20 μM or higher. Receptors of 10 μM concentration or higher were separately prepared bound to agonist.

To prepare complex, agonist-bound receptor was mixed with a stoichiometric excess of G protein (typically 1.5 to 2 fold molar excess) at room temperature, and magnesium chloride was added to a concentration of 1-10 mM. This reaction was incubated for 30 minutes at room temperature. Following incubation, 0.5-10 milliunits apyrase was added to the reaction, which was then incubated for an additional 30 minutes at room temperature. The complex, once prepared, was typically stable on ice for several hours. Apyrase can be inhibited with the addition of EDTA, if needed. Specific examples follow:

$M_3$ Muscarinic Receptor:Gq
- 5 µL $M_3$ 263C bound to iperoxo and biotinylated on Cys263 with PEG11-biotin maleimide (65 µM receptor stock)
- 2.5 µL Gq heterotrimer (230 µM stock)
- 0.5 µL 50 mM $MgCl_2$
- 0.5 µL iperoxo 1 mM
- Incubate 30 min at room temperature, then add apyrase (1 milliunit)
- Incubate 30 min at room temperature, then store on ice.

Protease Activated Receptor 1:Gi
- Pretreat receptor with 1 µL (0.1 U) of 10-fold diluted thrombin for 30 min. at room temperature
- 10 µL PAR1 with labeled with Alexa 647 (87 µM stock of receptor)
- 10 µL Gi heterotrimer (170 µM)
- 1 µL 50 mM $MgCl_2$
- Incubate 30 min at room temperature, then add apyrase (1 milliunit)
- Incubate 30 min at room temperature, then store on ice.

$\beta_2$ Adrenoceptor:Gs
- Pretreat receptor with 40 µM BI167107 for 30 min at room temperature
- 50 µL $\beta_2$-biotin (20 µM stock)
- 10 µL Gs heterotrimer (170 µM stock)
- 0.5 µL 2 M $MgCl_2$
- Incubate 30 min at room temperature, then add apyrase (1 milliunit)
- Incubate 30 min at room temperature, then store on ice.

Mu Opioid Receptor (MOR):Gi
- Pretreat receptor with 150 µM of agonist $DMT^1$-DALDA for 30 min at room temperature
- 10 µL MOR labeled with Alexa 647 (100 µM stock)
- 10 µL Gi heterotrimer (170 µM stock)
- 1 µL 50 mM $MgCl_2$
- Incubate 30 min at room temperature, then add apyrase (1 milliunit)
- Incubate 30 min at room temperature, then store on ice.

All dilutions were prepared in a buffer consisting of 100 mM sodium chloride, 20 mM HEPES pH 7.5, 0.1% DDM, 0.01% CHS.

For preparation of complex on cells (i.e., when cells are expressing potential ligands), the following procedure may be used:

Cells are first labeled with purified, unliganded receptor for one hour at 4° C. in a suitable buffer (e.g., phosphate buffered saline with 0.5 mg/mL BSA and 0.1% DDM; PBD buffer). Unbound receptor is then removed by washing the cells, which are then stained with purified, distinguishably-labeled heterotrimeric G protein for 30 minutes at room temperature in the presence 1 mM magnesium chloride. On-cell complexes are stabilized by the addition of 1 milliunit apyrase per milliliter of volume and further incubation for 30 minutes.

Results I

To test the possibility of using yeast display to select conformationally-specific GPCR binding proteins, Nb80 was displayed on yeast. Nb80 is a previously described camelid heavy chain antibody variable fragment that specifically binds the $\beta_2$ receptor when it is occupied with agonist (Steyaert et al Curr. Opin. Struct. Biol. 2011 21: 567-572). As shown in FIG. 5, the $\beta_2$ receptor binds strongly to Nb80-expressing yeast when receptor is bound to the full agonist BI-167107, but only a small amount of non-specific staining occurs with receptor bound to the inverse agonist/antagonist carazolol. Nb80 is a previously published active-state GPCR binder.

Figure 6:
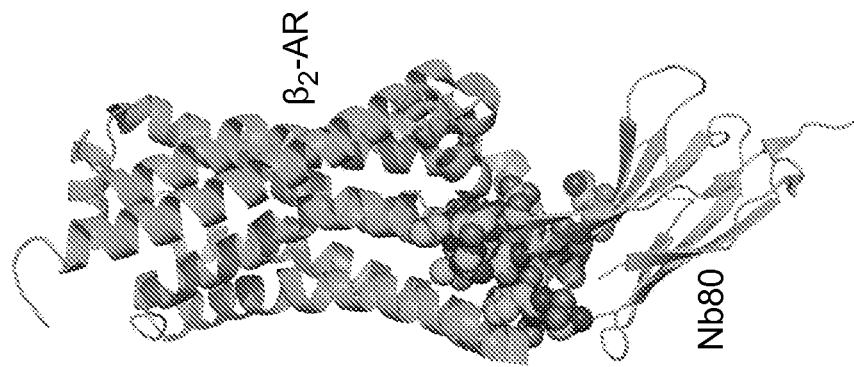
FIG. 6 shows the library design for Nb80 affinity maturation.
Figure 7:
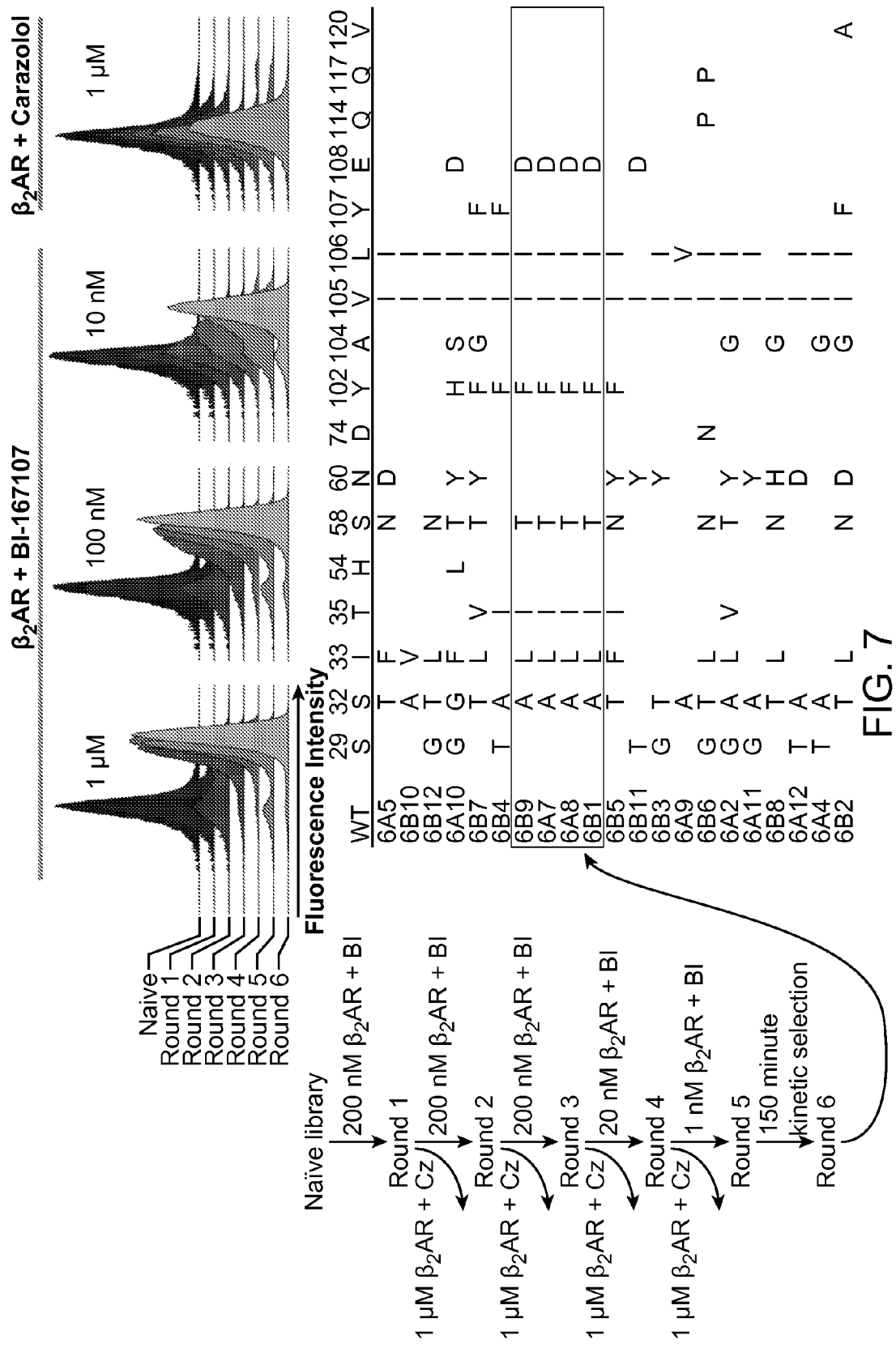
FIG. 7 shows results of selection from the Nb80SR library.

A library of Nb80 variants was designed in which each contact residue was randomized to four possibilities: wild-type and three conservative substitutions (shown in FIG. 6). The library was transformed in yeast and selected for binding to the $\beta_2$ receptor occupied by agonist BI-167107 using the method shown at the left of FIG. 7. This selection was done entirely by magnetic cell sorting (MACS), selecting each round with agonist-bound receptor after first counter-selecting with antagonist bound receptor. The selection process was repeated with decreasing concentrations of receptor to isolate high affinity binders. The staining of the library as a whole is plotted (FIG. 7 upper right) as a function of selection round. Although the staining with agonist-bound $\beta_2$ receptor increases each round, staining with antagonist-occupied receptor is kept low through negative selection. The sequences of resulting clones are shown at lower right of FIG. 7. Eight mutations which give high affinity binding were identified.

Figure 8:
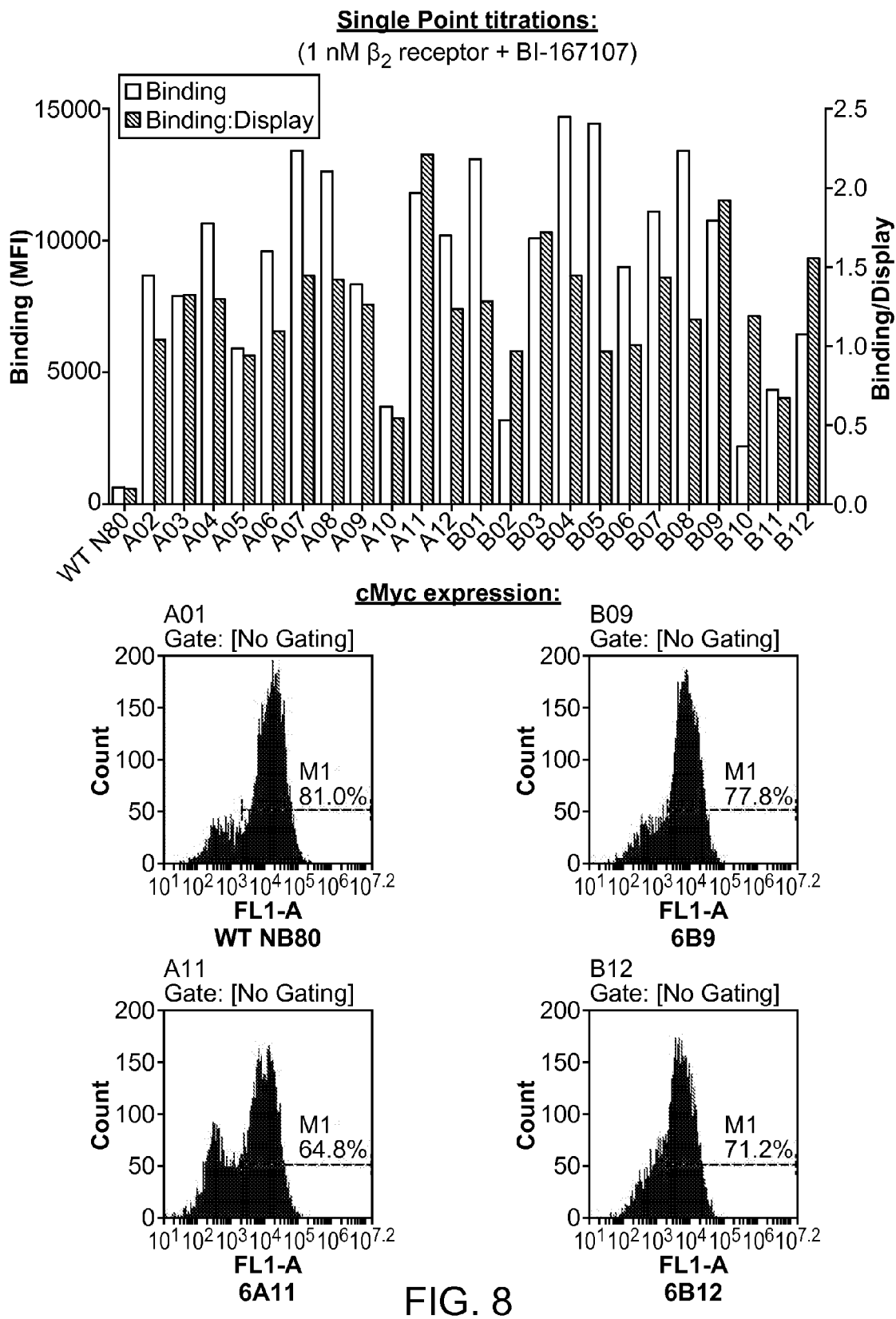
FIG. 8 shows results of $\beta_2$ adrenergic receptor binding to selected yeast variants.

To select the highest affinity clone, 1 nM receptor of the $\beta_2$ receptor was test tested for staining. Those clones with high staining (after correction for expression level) were chosen for further characterization (FIG. 8, left hand side). Expression for several clones (indicated by cMyc staining) was similar (FIG. 8, right), confirming that higher staining results from higher affinity rather than simply more abundant nanobodies.

Figure 9:
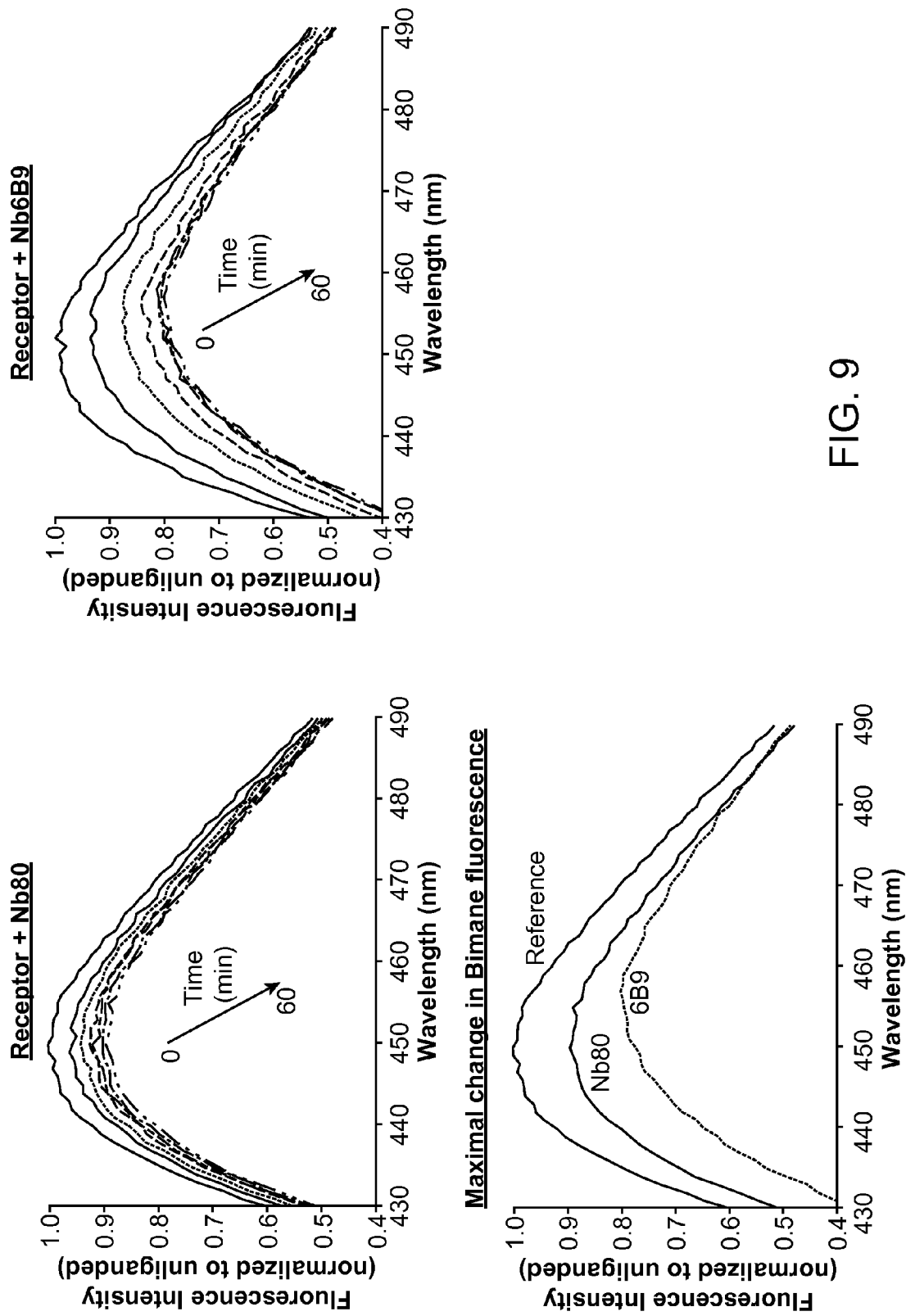
FIG. 9 shows the results of bimane assays of $\beta_2$ adrenergic receptor in the presence of Nb80 or Nb6B9.
Figure 10:
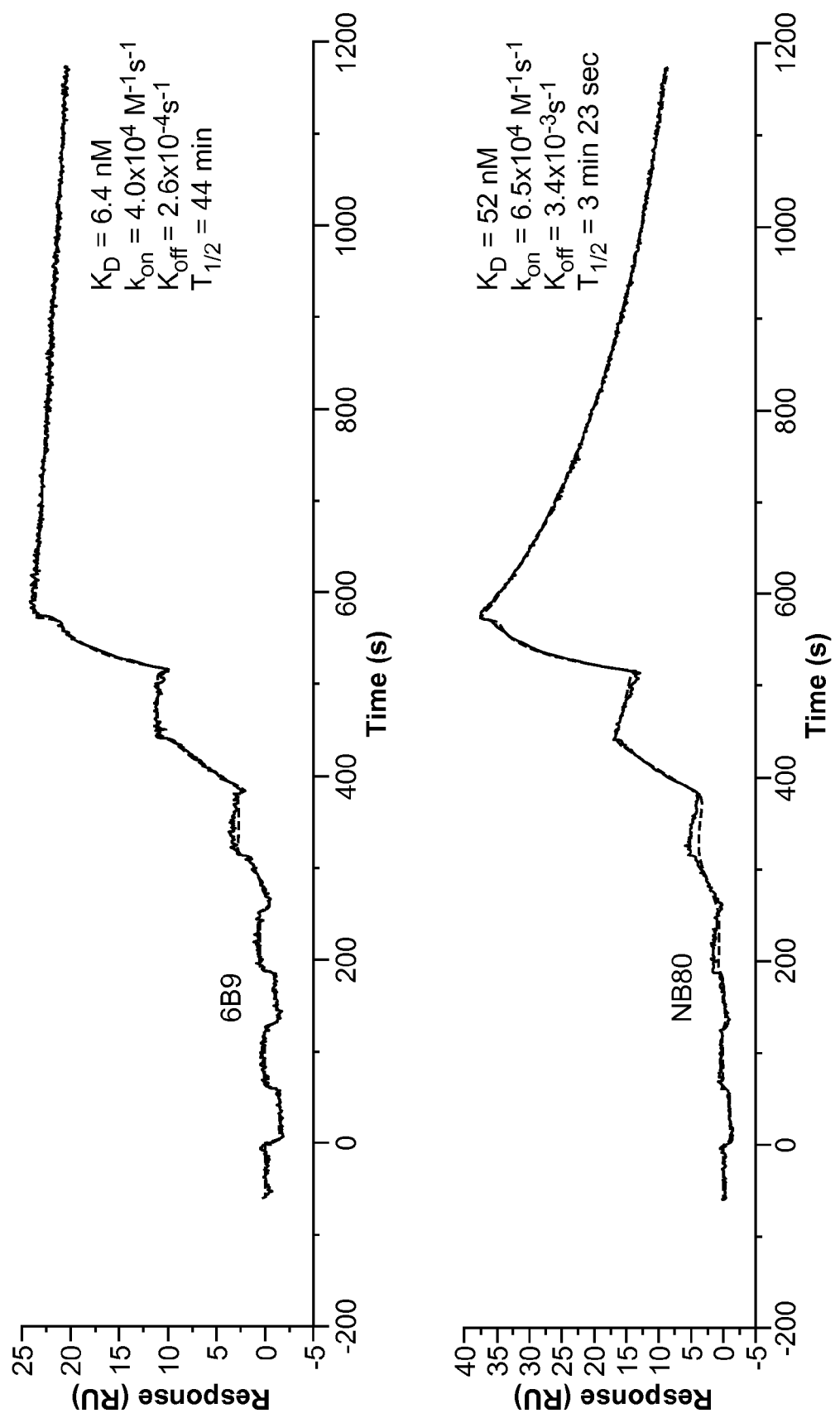
FIG. 10 shows the results of affinity measurements for Nb6B9 and Nb80.

To determine whether the $\beta_2$ receptor conformation is stabilized by the selected nanobodies, a bimane fluorescence assay was performed (FIG. 9). This is an established technique to measure $\beta_2$ receptor activation. The curve shifts down and left when the receptor is in the active state. As shown in FIG. 9 (upper left), on unliganded receptor, Nb80 is able to cause a slight downshift. This indicates that a small amount of receptor is being trapped in the active state by this lower affinity binder. Nb6B9 induces a stronger response in this assay, indicating that it is more effective at trapping $\beta_2$ receptors in an active conformation (FIG. 9 upper right; lower left). FIG. 10 shows the results of affinity measurements for Nb6B9. Affinity and binding kinetics of wild-type Nb80 and the new, high affinity variant Nb6B9 were measured by surface plasmon resonance. Binding parameters are shown at right, showing a greater than ten-fold slowing of dissociation.

Methods II $M_2$ Muscarinic Receptor Expression and Purification.

Human $M_2$ muscarinic receptor bearing an amino-terminal FLAG epitope tag and carboxy-terminal 8xHis tag was expressed in Sf9 cells using the BestBac baculovirus system (Expression Systems; Davis, Calif.). Cells were infected at a density of $4\times10^6$ cells/mL, then incubated for two days at 27° C. Receptor was extracted and purified in the manner described previously for the $M_3$ muscarinic receptor[1]. Briefly, receptor was first purified by Ni-NTA chromatography, FLAG affinity chromatography, then size exclusion chromatography. 1 µM atropine was included in all buffers.

Receptor was then labeled with a 5-fold molar excess of biotin-NHS ester (Sigma-Aldrich; St. Louis, Mo.) in buffer containing 25 mM HEPES pH 7.2. Following a 30 minute incubation at room temperature and a 30 minute incubation on ice, unreacted label was quenched with 50 mM tris pH 8. Directly labeled samples with fluorophore-NHS esters were prepared similarly. Receptor was then desalted into buffer containing either 10 µM tiotropium, 10 µM iperoxo, or buffer containing no ligand. Receptor eluted in buffer containing no ligand was treated with 50 µM iperoxo mustard for 20 minutes at room temperature. Samples were then concentrated, aliquoted, and flash frozen with 20% (v/v) glycerol.

Llama Immunization Samples.

$M_2$ receptor was prepared as described above, and bound to iperoxo. Receptor was reconstituted in vesicles of DOPC/CHS and lipid A, then aliquoted at 1 mg/mL receptor concentration and frozen in 100 µL aliquots prior to injection.

Post-Immune $M_2$ Llama Nanobody Library Construction.

A cDNA pool was prepared from llama B cells following immunization with M2 receptor, as described in Rasmussen et al (Nature 2011, 469, 175-180). Nanobody $V_{HH}$ fragments were amplified by PCR using the primers pYa1NB80AMPF and pYa1NB80AMPR. The PCR products were then co-transformed with linearized pYal into yeast strain EBY100 as for the Nb 80 affinity-maturation library, yielding a library size of $0.6 \times 10^8$ transformants.

Selections of $M_2$ $G_i$-Mimetic Nanobodies from Post-Immune $M_2$ Llama Nanobody Library.

For the first round of selection, counter-selection was performed against the $\beta_2$ receptor to remove yeast-clones that bind non-specifically to membrane proteins or to secondary staining reagents. $1.0 \times 10^9$ of induced yeast were washed with PBEM buffer and then stained in 5 mL of PBEM buffer containing 1 µM biotinylated $\beta_2$ receptor liganded with carazolol for one hour at 4° C. Yeast were then stained with streptavidin-647 as a secondary reagent and magnetically-labeled with anti-647 microbeads (Miltenyi) as for the Nb80 affinity-maturation library selections. Positively labeled yeast were then removed by application to an LD column (Miltenyi); the cleared flow-through was then used for subsequent selection. Positive selection for clones recognizing the active-state of the $M_2$ receptor was performed by staining the yeast with 2 µM biotinylated $M_2$ receptor liganded with the agonist iperoxo in 5 mL PBEM buffer supplemented with 2 µM iperoxo for one hour at 4° C. Yeast were then washed, stained with streptavidin-647, and magnetically-labeled with anti-647 microbeads, including 1 µM iperoxo in the PBEM buffer at all steps. Magnetic separation of $M_2$ receptor-binding yeast was performed using an LS column (Miltenyi) following the manufacturer's instructions. Magnetically sorted yeast were resuspended in SDCAA medium and cultured at 30° C. Rounds 2-4 were selected in a similar manner, counter-selecting against 1 µM biotinylated $\beta_2$ receptor+carazolol and positively selecting using 1 µM biotinylated $M_2$ receptor+iperoxo. For these rounds, the scale was reduced ten-fold to $1 \times 10^8$ induced yeast and staining volumes of 0.5 mL.

Conformational selection was performed for rounds 5-9. For rounds 5-8, yeast were stained with 1 µM biotinylated $M_2$ receptor pre-incubated with the high-affinity antagonist tiotropium for one hour at 4° C. Yeast were then fluorescently labeled with either streptavidin-647 or streptavidin-PE, and magnetically labeled with the corresponding anti-647 or anti-PE microbeads (Miltenyi). Depletion of inactive-state binders was carried out using an LS column. The cleared yeast were then positively selected by staining with 0.5 µM (rounds 5-7) or 0.1 µM (round 8) $M_2$ receptor pre-bound to with iperoxo for one hour at 4° C. Yeast were then fluorescently-labeled with either streptavidin-PE or streptavidin-647, using the fluorophore distinct from counter-selection in the previous step. Magnetic separation of agonist-occupied $M_2$ receptor was performed using an LS column, as for steps 1-4. For round 9, two-color FACS was performed. Induced yeast were simultaneously stained with 1 µM Alexa647-labeled $M_2$ receptor reacted with iperoxo mustard and 1 µM Alexa488-labeled $M_2$ receptor pre-bound with tiotropium for one hour at 4° C. Alexa647 positive/Alexa488 negative yeast were purified using a FACS Jazz cell (BD Biosciences) sorter. Post-sorted yeast were plated onto SDCAA-agar plates and the nanobody-encoding sequences of several colonies were sequenced, as described for the Nb80 selections.

Selections of Functional Nanobodies with $M_2$ $G_i$ Mimetic Nanobody Nb9-8.

Selections were initiated with the yeast remaining after the first four rounds of selection for the M2 $G_i$ mimetic nanobody prior to conformational selection. For rounds 5 & 6, yeast were precleared using MACS against 500 nM PE-labeled streptavidin tetramers conjugated to biotinylated Nb9-8, removing clones that bind Nb9-8 directly. Tetramers were formed by pre-incubating 2 µM biotinylated Nb9-8 with 0.5 µM streptavidin-PE in PBEM buffer on ice for 10 minutes. The yeast were then positively selected with 500 nM streptavidin-PE/Nb9-8 tetramers after first staining the yeast with 1 µM Alexa488-labeled $M_2$ receptor reacted with iperoxo mustard. Magnetic separation with MACS was accomplished using anti-PE microbeads and an LS column. To further select for clones binding at extracellular, allosteric/orthosteric site of the $M_2$ receptor, for rounds 7 and 8 counter-selection was performed against 1 µM biotinylated $M_2$ receptor occupied with iperoxo in the presence of 2 mM of the allosteric/orthosteric ligand gallamine. Positive selection for $M_2$ receptor in the absence of gallamine was then performed using 1 µM biotinylated $M_2$ receptor occupied with iperoxo and MACS for round 7 and 1 µM Alexa488-labeled $M_2$ receptor reacted with iperoxo mustard and FACS for round 8.

Expression of MBP-Nanobody Fusions in *E. coli*.

Nanobody sequences were subcloned into a modified pMalp2× vector (New England Biolabs), containing an amino-terminal, 3C protease-cleavable maltose binding protein (MBP) tag and a carboxy-terminal 8×Histidine tag. Plasmids were transformed into BL21(DE3) cells and protein expression induced in Terrific Broth by addition of IPTG to 1 mM at an $OD_{600}$ of 0.8. After 24 hours of incubation at 22° C., cells were harvested and periplasmic protein obtained by osmotic shock. MBP-nanobody fusions were purified by Ni-NTA chromatography and MBP was removed using 3C protease. Cleaved MBP was separated from the 8×His tagged nanobodies by an additional Ni-NTA purification step. The 8×His tag was subsequently removed using carboxypeptidase A. To obtain biotinylated nanobodies, proteins were expressed with a carboxy-terminal biotin acceptor peptide tag (GLNDIFEAQKIEWHE, SEQ ID NO:32) and purified as described above. The purified proteins were biotinylated in vitro with BirA ligase and then repurified from the reaction mixture by size exclusion chromatography.

$M_2$ Receptor Radioligand Binding Assays.

$M_2$ receptor was expressed and purified as described above. Receptor was then reconstituted into HDL particles consisting of apolipoprotein A1 and a 3:2 (mol:mol) mixture of the lipids POPC:POPG. Binding reactions contained 50 fmol functional receptor, 0.6 nM $^3$H N-methyl scopolamine (NMS), 100 mM NaCl, 20 mM HEPES pH 7.5, 0.1% BSA, and ligands and nanobodies as indicated. Single point allosteric effects of nanobodies were measured in the presence of 10 nM iperoxo. All reactions were 500 µL in volume. Reactions were mixed and then incubated for two hours. Samples were then filtered on a 48-well harvester (Brandel) onto a filter which had been pre-treated with 0.1% polyethylenimine. All measurements were taken by liquid scintillation counting, and experiments were performed at least in triplicate.

Results II

To extend the yeast display approach to another membrane protein, conformationally specific, $G_i$ mimetic proteins were identified for the $M_2$ muscarinic receptor. A post-immune library of llama nanobody variants was displayed on the surface of yeast and selected for the ability to bind to the $M_2$ receptor occupied with an agonist, iperoxo. Four rounds of selections were first performed by MACS, selecting each round with agonist-bound receptor after first counter-selecting against an unrelated membrane protein ($\beta_2$ adrenergic receptor). This was followed by several rounds of conformational selection using MACS where the yeast were first counter-selected against inverse agonist (tiotropium)-occupied $M_2$ receptor followed by positive selection with agonist (iperoxo)-occupied $M_2$ receptor. For the ninth and final round of selection, a FACS-based selection was employed. Yeast were simultaneously stained with Alexa647-labeled M2 receptor bound with the covalent agonist iperoxo mustard and with Alexa488-labeled M2 receptor bound to tiotropium. Yeast positive only for 647 were purified, thus selecting those variants preferentially binding agonist-occupied receptor.

Figure 11:
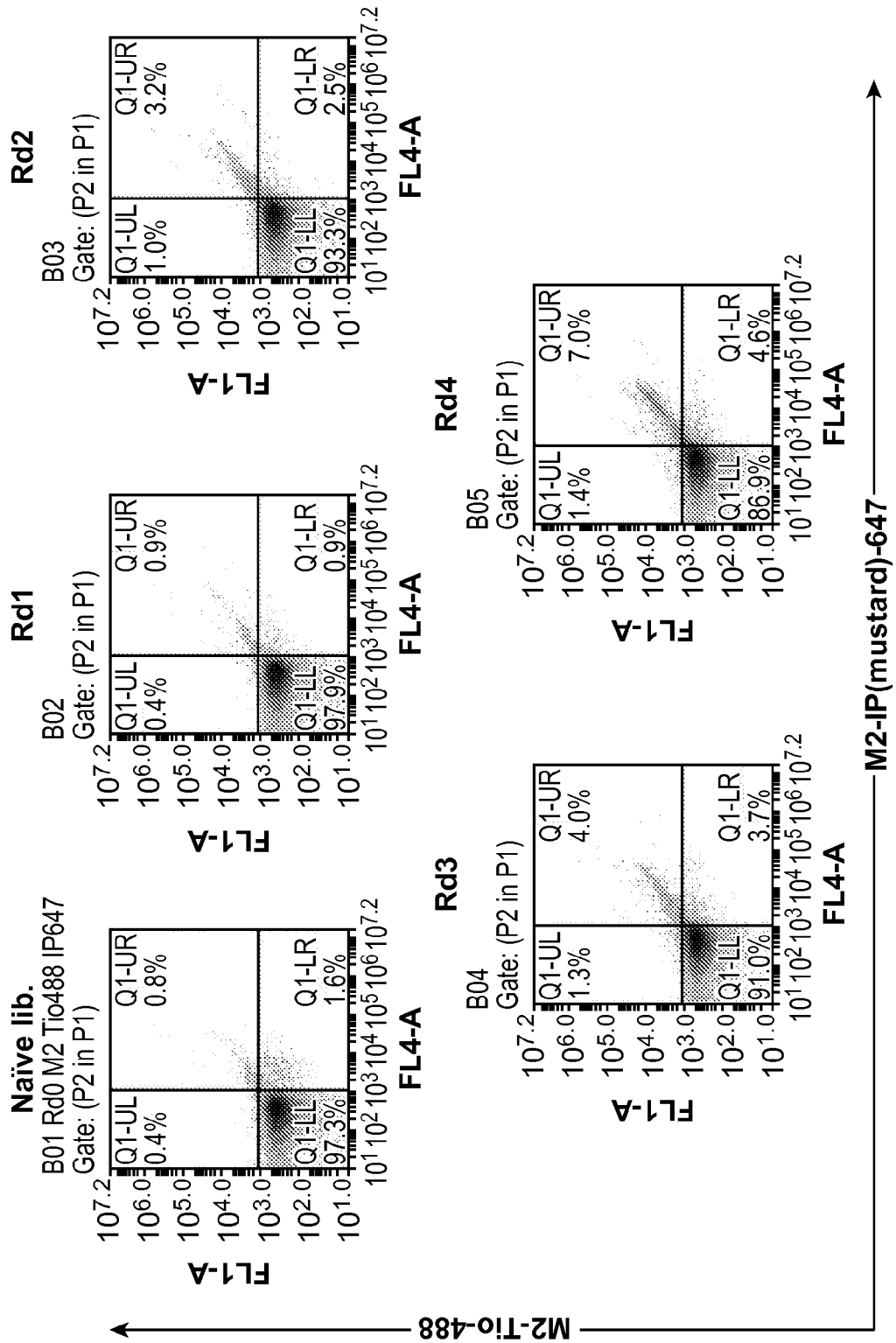
FIG. 11 shows results of selection of $M_2$ $G_i$ mimetic nanobodies from a post-immune llama $V_{HH}$ library.
Figure 11:
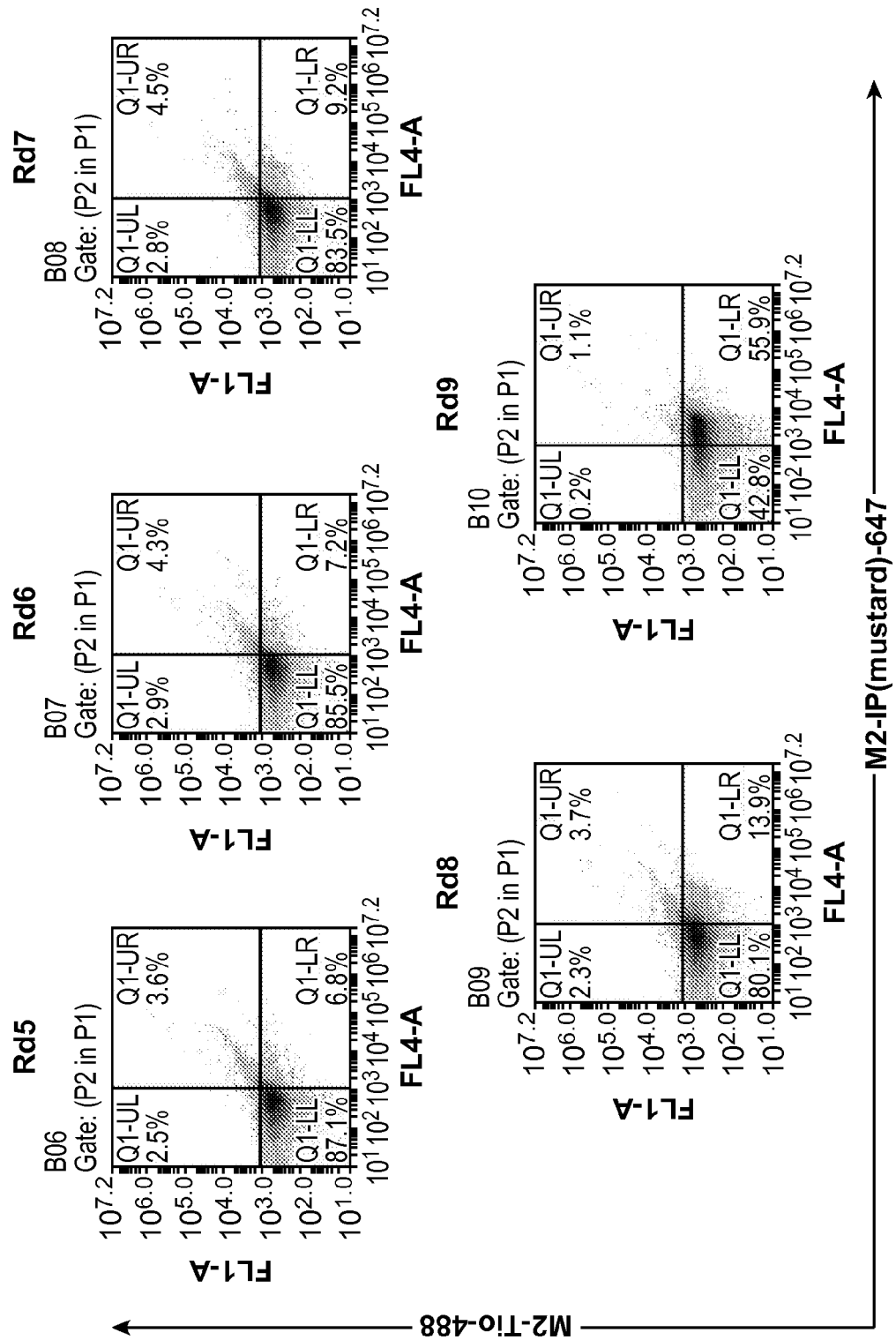
Figure 12:
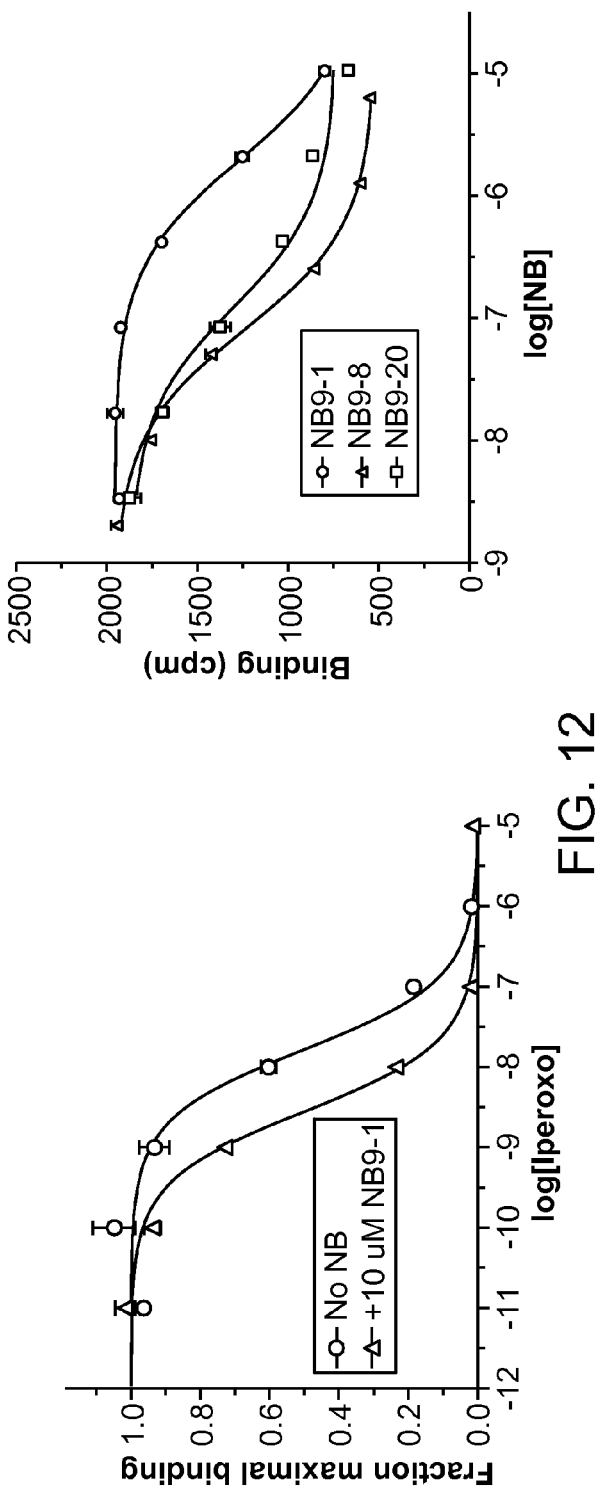
FIG. 12 summarizes sequences of selected $M_2$ $G_i$ mimetics and shows their effect on an M2 receptor radioligand binding assay (From top to bottom SEQ ID NOs:13-23).

The staining of the library during the selection process as a whole shows enrichment of nanobody variants that bind to $M_2$ receptor occupied by the agonist iperoxo, but not to $M_2$ receptor bound to the inverse agonist tiotropium, particularly after applying conformational selection in rounds 5-9 (FIG. 11). To determine whether the nanobody variants that specifically stain agonist-bound $M_2$ receptor are able to stabilize the $M_2$ receptor active state, a binding assay was performed. Due to the allosteric properties of GPCRs, molecules that stabilize the active conformation of a receptor also increase agonist affinity. Several conformationally specific binders were isolated and were tested for their ability to induce an increase in the affinity of the non-covalent agonist iperoxo. Results for one of these, nanobody clone Nb9-1, are shown in FIG. 12. Furthermore, Nb9-1 and other conformationally specific binders displayed a dose-dependent effect on agonist ability to displace a radioactive probe (FIG. 12). Among these, clone Nb9-8 showed the highest affinity.

Figure 13:
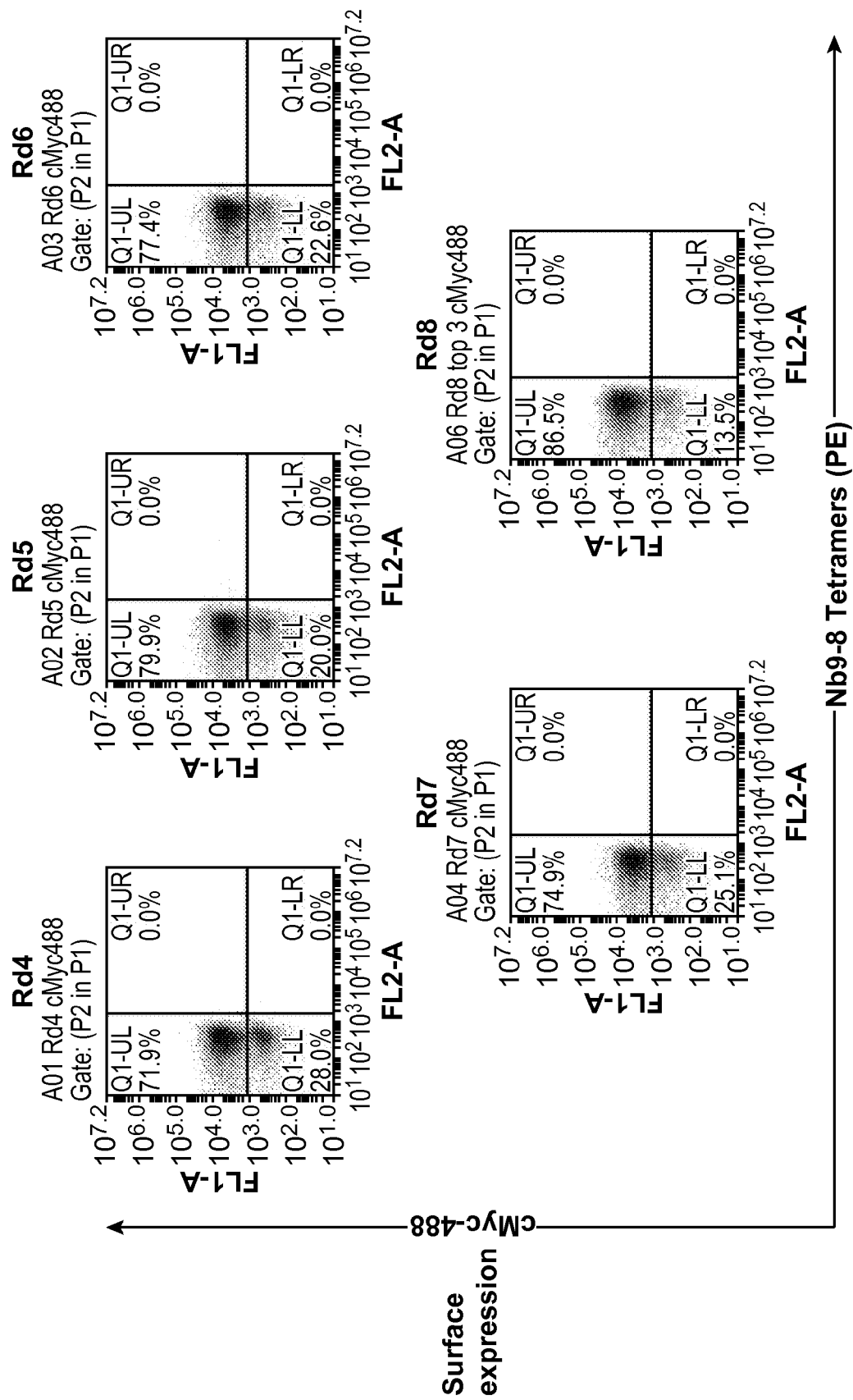
FIG. 13 shows results of selections for functional $M_2$ nanobody ligands from a post-immune llama $V_{HH}$ library using the $G_i$, mimetic Nb9-8.

To select for functional ligands to the $M_2$ receptor, the library resulting from the first four rounds of MACS selection described above was subjected to further selections to identify nanobody variants that bind to the extracellular side of the receptor. First, two rounds of MACS selections were performed by selecting for the ability of variants to recruit Nb9-8 in the presence of $M_2$ receptor, while counter-selecting for variants that bind to Nb9-8 in the absence of the $M_2$ receptor. This selection strategy enriches for clones that either induce or are compatible with an active conformation of the $M_2$ receptor, but that also bind to a site distinct from that of Nb9-8. To further select for variants that bind specifically to the extracellular side of the $M_2$ receptor, counter-selection was performed against $M_2$ receptor in the presence of the allosteric muscarinic ligand gallamine, while positively selecting those clones binding $M_2$ receptor in the absence of gallamine. The staining of the selection process as a whole shows enrichment of nanobody variants that bind to the $M_2$ receptor and Nb9-8 simultaneously (FIG. 13). Furthermore, these clones are sensitive to the presence of gallamine, suggesting that they bind at the allosteric/orthosteric site of the receptor. The allosteric binding properties of several of these clones were measured by a binding assay (FIG. 14). Among the characterized variants, clone B4 and others caused a decrease in the binding of the radioligand N-methylscopolamine only in the presence of agonist, consistent with the ability of the clone to bind at the allosteric site of the $M_2$ receptor.

FIG. 15 shows additional characterization of the allosteric effect of nanobodies NbB4 and NbA2 isolated using M2 receptor and Gi mimetic 9-8.

Top: the competition radioligand binding experiment described in FIG. 14 was repeated, using a fixed concentration of Nb9-8, NbA2, and NbB4 (called NbExtA2 and NbExtB4 in the figure), and titrating increasing concentrations of acetylcholine (ACh) to measure the shift in the receptor affinity for agonist (ACh) compared to probe antagonist (NMS). Each nanobody demonstrated positive allosteric modulation of the M2R.

Bottom: iPS-derived human myocytes were subjected to varying concentrations of the M2R agonist iperoxo in the presence or absence of NbB4 and NbA2. Upon activation, the M2 receptor activates the inhibitory G-protein Gi in myocytes and decreases beating frequency. In this assay, NbB4 and NbA2 increased the potency of iperoxo to slow the myocyte beating rate.

What is claimed is:

1. A method comprising:
   (a) producing: (i) a transmembrane receptor in an active conformation; and
      (ii) the same transmembrane receptor in an inactive conformation; and
   (b) using cell sorting to select, from a population of cells comprising a library of cell surface-tethered extracellular capture agents, cells that are selectively bound to either the transmembrane receptor in its active conformation or the transmembrane receptor in its inactive conformation, but not cells that bind to both the active and inactive conformations of the transmembrane receptor.

2. The method of claim 1, wherein the transmembrane receptor in the active conformation of (a)(i) and the transmembrane receptor in the inactive conformation of (a)(ii) are distinguishably tagged; and step (b) comprises:
   (i) combining, under binding conditions, the distinguishably tagged proteins with the population of cells; and
   (ii) using cell sorting to select cells produced by step (b) that are specifically bound to either the transmembrane receptor in its active conformation or the transmembrane receptor in its inactive conformation, but not cells that bind to both the active and inactive conformations of the transmembrane receptor.

3. The method of claim 1, wherein
   the transmembrane receptor in its active conformation of (a) (i) and the transmembrane receptor in its inactive conformation of (a) (ii) are distinguishably tagged by:
   (i) combining a first portion of a sample comprising said transmembrane receptor with an agonist to place said transmembrane receptor in its active conformation, and then labeling the active conformation transmembrane receptor with a first fluorescent label: and
   (ii) combining a second portion of the sample with an antagonist to place said transmembrane receptor in its inactive conformation, and then labeling the inactive conformation transmembrane receptor with a second fluorescent label that is distinguishable from the first fluorescent label;
   and said cell sorting step (c) is done by fluorescence activated cell sorting (FACS).

4. The method of claim 1, wherein the transmembrane receptor in its active conformation of (a) (i) and the transmembrane receptor in its inactive conformation of (a) (ii) are distinguishably tagged using different epitope tags.

5. The method of claim 1, wherein step (b) comprises:
   (i) using cell sorting to select, from an initial population of cells, a sub-population of cells that bind to only one of the transmembrane receptor conformations of step (a); and
   (ii) using cell sorting to remove, from said sub-population of cells, cells that bind to the other of said conformations of step (a).

6. The method of claim 1, wherein step (b) comprises:
   (i) using cell sorting to select, from an initial population of cells, a sub-population of cells that do not bind to one of the transmembrane receptors of step (a); and
   (ii) using cell sorting to select, from said sub-population of cells, cells that bind to the other of said proteins of step (a).

7. The method of claim 1, wherein said transmembrane receptor is a GPCR, an ion channel, a member of the PAQR (Progestin and AdipoQ Receptor) family, an adiponectin receptor, or a carrier transporter.

8. The method of claim 1, wherein said transmembrane receptor is a GPCR (G protein-coupled receptor).

9. The method of claim 1, wherein said using cell sorting step (c) is done using FACS (fluorescence activated cell sorting) or MACS (magnetic activated cell sorting).

10. The method of claim 1, wherein said population of cells is a population of yeast cells.

11. The method of claim 1, wherein the capture agents are single chain antibodies.

12. The method of claim 11, wherein said antibodies are encoded by cDNAs obtained from an animal that has been immunized with said transmembrane receptor in its active or inactive conformation.

13. The method of claim 12, wherein said animal is a camelid.

14. The method of claim 1, wherein said library of cell surface-tethered extracellular capture agents is a library of variants of a binding agent that is known to bind said transmembrane receptor in its active or inactive conformation and not bind both the active and inactive conformations of the transmembrane receptor.

15. The method of claim 1, wherein at least said step (b) is repeated multiple times to remove false positives and/or false negatives.

16. The method of claim 1, wherein said method comprises isolating a nucleic acid encoding at least the binding region of the cell surface-tethered extracellular capture agent from a cell sorted in step (b).

17. The method of claim 16, wherein said method comprises expressing the binding region of the cell surface-tethered extracellular capture agent in a second host cell.

18. The method of claim 17, further comprising measuring the affinity of said binding region to a transmembrane receptor in its active or inactive conformation relative to the same transmembrane receptor in the other conformation.

19. The method of claim 2, wherein the distinguishably tagged proteins of step (a) are detergent solubilized.

20. A method comprising:
(a) contacting a GPCR with a population of cells that comprise a library of surface-tethered extracellular proteins;
(b) labeling the cell population of (a) with a G-protein or mimetic thereof that specifically binds to said GPCR in its active or inactive state; and
(c) using cell sorting to select from the cell population of (c) cells that bind to the G-protein or mimetic thereof.

21. The method of claim 20, wherein the G-protein or mimetic thereof is labeled prior to step (b) or between steps (b) and (c).

22. The method of claim 21, wherein G-protein or mimetic thereof is labeled with a fluorophore or using a labeled antibody.

23. The method of claim 20, wherein said labeled G-protein is a heterotrimer G-protein comprising $G_s$, $G_i$, $G_q$, $G_{12}$ or $G_t$, in the presence of GDP.

24. The method of claim 20, wherein said mimetic is an antibody.

25. The method of claim 20, wherein said library of surface-tethered extracellular proteins is a library of surface tethered peptides.

26. The method of claim 20, wherein said cell sorting is by FACS or MACS.

27. The method of claim 20, wherein said cell population of (b) is a population of yeast cells.

28. The method of claim 20, wherein said method comprises isolating a nucleic acid encoding at least the binding region of the cell surface-tethered extracellular protein from a cell sorted in step (c).

29. The method of claim 28, wherein said method comprises expressing the binding region of the cell surface-tethered extracellular protein in a second host cell.

30. The method of claim 29, further comprising determining whether said binding region is an agonist or antagonist of said GPCR.

* * * * *